(12) United States Patent
Lane et al.

(10) Patent No.: US 10,006,078 B2
(45) Date of Patent: *Jun. 26, 2018

(54) USE OF PHOSPHO-AKT AS A BIOMARKER OF DRUG RESPONSE

(75) Inventors: Heidi Alexandra Lane, Therwil (CH); Felix Bachmann, Basel (CH)

(73) Assignee: BASILEA PHARMACEUTICA AG, Basel (CH)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/005,680

(22) PCT Filed: Mar. 28, 2012

(86) PCT No.: PCT/EP2012/055522
§ 371 (c)(1),
(2), (4) Date: Dec. 4, 2013

(87) PCT Pub. No.: WO2012/130887
PCT Pub. Date: Oct. 4, 2012

(65) Prior Publication Data
US 2014/0080872 A1    Mar. 20, 2014

(30) Foreign Application Priority Data
Mar. 29, 2011 (EP) .................................... 11160275

(51) Int. Cl.
| | | |
|---|---|---|
| *A61K 31/4245* | (2006.01) | |
| *A61K 31/4439* | (2006.01) | |
| *C12Q 1/48* | (2006.01) | |
| *G01N 33/574* | (2006.01) | |
| *C07D 413/04* | (2006.01) | |
| *C07D 413/14* | (2006.01) | |

(52) U.S. Cl.
CPC ........... *C12Q 1/485* (2013.01); *C07D 413/04* (2013.01); *C07D 413/14* (2013.01); *G01N 33/57407* (2013.01); *G01N 2440/14* (2013.01); *G01N 2800/52* (2013.01)

(58) Field of Classification Search
CPC .............. C07D 413/04; A61K 31/4245; A61K 31/4439
USPC .................................................. 514/364, 338
See application file for complete search history.

(56) References Cited

U.S. PATENT DOCUMENTS 7,385,061 B2 * 6/2008 Eberle .................. C07D 413/14
548/125

FOREIGN PATENT DOCUMENTS

| WO | 2004103994 A1 | 12/2004 |
|---|---|---|
| WO | WO 2004103994 A1 * | 12/2004 |
| WO | 2010135671 A1 | 11/2010 |
| WO | 2011012577 A1 | 2/2011 |

OTHER PUBLICATIONS

Han, H.K. "Targeted Prodrug Design to Optimize Drug Delivery." AAPS Pharmsci. (2000), vol. 2 (1) article 6, pp. 1-11.*
Ettmayer, P., et al. "Lessons Learned from Marketed and Investigational Prodrugs." J. Med. Chem. (2004) 47(10), pp. 2393-2404.*
Testa, B. "Prodrug research: futile or fertile?" Biochem. Pharm. (2004) 68, pp. 2097-2106.*
VanderWeele et al., "Akt up-regulation increases resistance to microtubule-directed chemotherapeutic agents through mammalian target of rapamycin," Molecular Cancer Therapeutics 3(12), pp. 1605-1613 (2004).
Ching et al., "Expanding therapeutic targets in bladder cancer: the PI3K/Akt/mTOR pathway," Laboratory Investigation 90, pp. 1406-1414 (2010).
Duran et al., AACR 101st Annual Meeting Apr. 17-21, Abstract of poster No. 4412, (2010).
McGrogan et al., "Taxanes, microtubules and chemoresistant breast cancer," Biochim. Biophys. Acta 1785, pp. 96-132 (2008).
Bandarage et al., "4-(Benzimidazol-2-yl)-1,2,5-oxadiazol-3-ylamine derivatives: Potent and selective p70S6 kinase inhibitors," Bioorganic & Medicinal Chemistry Letters 19, pp. 5191-5194 (2009).
Weng et al., "Implication of the Akts/survivin pathway as a critical target in paclitaxel treatment in human ovarian cancer cells," Cancer Letters 273, pp. 257-265 (2009).
The International Search Report and Written Opinion, dated May 7, 2012, in the related PCT Appl. No. PCT/EP2012/055522.
Bachmann et al., "BAL27862: A Novel Anticancer Agent that Dissociates Microtubules and Creates a Distinct Cellular Phenotyp," EORTC-NCI-AACR Sympostium 2009, Abstract No. C229, Poster.
Duran et al., "In vitro activity of the novel tubulin active agent BAL27862 in MDR1(+) and MDR1(-) human breast and ovarian cancer variants selected for resistance to taxanes," AACR 101st meeting, Apr. 17-21, 2010, Poster.
F. Bachmann et al: 'Abstract C229: BAL27862: A novel anticancer agent which dissociates microtubules and creates a distinct cellular phenotype' Poster on AACR-NCI-EORTC International Conference: Molecular Targets and Cancer Therapeutics—Nov. 15-19, 2009; Boston, MA Nov. 15, 2009.

* cited by examiner

*Primary Examiner* — Charanjit Aulakh
*Assistant Examiner* — John S Kenyon

(57) ABSTRACT

Use of phospho-Akt as a biomarker for predicting the response, such as resistance, to a compound, wherein phospho-Akt is Akt that has been phosphorylated on one or more residues, with the proviso that for Akt1, Akt2, and Akt3 the designation phospho-Akt is used to indicate phosphorylation at a site other than T308, T309 or T305 respectively, wherein the compound is a compound of general formula (I).

81 Claims, 9 Drawing Sheets

Figure 9

Akt1 (RAC-alpha serine/threonine-protein kinase)
[Homo sapiens](SEQ. ID. No. 1)

```
  1 msdvaivkeg wlhkrgeyik twrpryfllk ndgtfigyke rpqdvdqrea plnnfsvaqc
 61 qlmkterprp ntfiirclqw ttviertfhv etpeereewt taiqtvadgl kkqeeeemdf
121 rsgspsdnsg aeemevslak pkhrvtmnef eylkllgkgt fgkvilvkek atgryyamki
181 lkkevivakd evahtltenr vlqnsrhpfl talkysfqth drlcfvmeya nggelffhls
241 rervfsedra rfygaeivsa ldylhseknv vyrdlklenl mldkdghiki tdfglckegi
301 kdgatmktfc gtpeylapev ledndygrav dwwglgvvmy emmcgrlpfy nqdheklfel
361 ilmeeirfpr tlgpeaksll sgllkkdpkq rlgggsedak eimqhrffag ivwqhvyekk
421 lsppfkpqvt setdtryfde eftaqmitit ppdqddsmec vdserrphfp qfsysasgta
```

Figure 10

Akt2 (RAC-beta serine/threonine-protein kinase) [Homo sapiens](SEQ. ID. No. 2)

```
  1 mnevsvikeg wlhkrgeyik twrpryfllk sdgsfigyke rpeapdqtlp plnnfsvaec
 61 qlmkterprp ntfvirclqw ttviertfhv dspdereewm raiqmvansl kqrapgedpm
121 dykcgspsds stteemevav skarakvtmn dfdylkllgk gtfgkvilvr ekatgryyam
181 kilrkeviia kdevahtvte srvlqntrhp fltalkyafq thdrlcfvme yanggelffh
241 lsrervftee rarfygaeiv saleylhsrd vvyrdiklen lmldkdghik itdfglckeg
301 isdgatmktf cgtpeylape vledndygra vdwwglgvvm yemmcgrlpf ynqdherlfe
361 lilmeeirfp rtlspeaksl lagllkkdpk qrlgggpsda kevmehrffl sinwqdvvqk
421 kllppfkpqv tsevdtryfd deftaqsiti tppdrydslg lleldqrthf pqfsysasir
481 e
```

Figure 11

Akt3 isoform 1 (RAC-gamma serine/threonine-protein kinase isoform 1) [Homo sapiens] (SEQ. ID. No. 3)

```
  1 msdvtivkeg wvqkrgeyik nwrpryfllk tdgsfigyke kpqdvdlpyp lnnfsvakcq
 61 lmkterpkpn tfiirclqwt tviertfhvd tpeereewte aiqavadrlq rqeeermncs
121 ptsqidnige eemdastthh krktmndfdy lkllgkgtfg kvilvrekas gkyyamkilk
181 keviiakdev ahtltesrvl kntrhpflts lkysfqtkdr lcfvmeyvng gelffhlsre
241 rvfsedrtrf ygaeivsald ylhsgkivyr dlklenlmld kdghikitdf glckegitda
301 atmktfcgtp eylapevled ndygravdww glgvvmyemm cgrlpfynqd heklfelilm
361 edikfprtls sdaksllsgl likdpnkrlg ggpddakeim rhsffsgvnw qdvydkklvp
421 pfkpqvtset dtryfdeeft aqtitititppe kydedgmdcm dnerrphfpq fsysasgre
```

USE OF PHOSPHO-AKT AS A BIOMARKER OF DRUG RESPONSE

This application is a National Stage Application of PCT/EP2012/055522 filed Mar. 28, 2012, which claims priority from European Patent Application 11160275.1 filed on Mar. 29, 2011. Each is incorporated by reference in its entirety.

The present invention relates to use of phospho-Akt as a biomarker for predicting the response of a disease, such as a neoplastic or autoimmune disease, preferably cancer, to a compound of general formula I, such as 3-(4-{1-[2-(4-amino-phenyl)-2-oxo-ethyl]-1H-benzoimidazol-2-yl}-furazan-3-ylamino)-propionitrile (BAL27862). In other aspects it relates to methods and kits, as well as methods of treatment involving the use of the biomarker.

Microtubules are one of the components of the cell cytoskeleton and are composed of heterodimers of alpha- and beta-tubulin. Agents that target microtubules are among the most effective cytotoxic chemotherapeutic agents having a broad spectrum of activity. Microtubule destabilising agents (e.g. the vinca-alkaloids such as vincristine, vinblastine and vinorelbine) are used for example in the treatment of several types of hematologic malignancies, such as lymphoblastic leukaemia and lymphoma, as well as solid tumours, such as lung cancer. Microtubule stabilising agents (e.g. the taxanes such as paclitaxel, docetaxel) are used for example in the treatment of solid tumours, including breast, lung and prostate cancer.

However resistance to these known microtubule targeting agents can occur. The resistance can either be inherent or can be acquired after exposure to these agents. Such resistance therefore impacts patient survival rates, as well as choices of treatment regimes. Several potential mechanisms of resistance have been identified, and include defects in the microtubule targets, such as elevated levels of beta-tubulin sub-type III and acquired mutations in beta-tubulin subtype I that are known to reduce taxane binding. Furthermore, defects in other cell proteins have been suggested to be associated with resistance to certain microtubule targeting agents, such as overexpression of the efflux pump P-glycoprotein (P-gp, also known as multi-drug resistance protein 1 or MDR1). Such factors may then be used as biomarkers of resistance to these conventional microtubule targeting agents.

A relatively recently discovered class of microtubule destabilising agents are compounds encompassed by the formula given below:

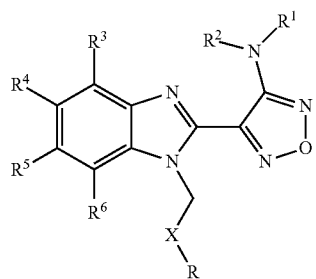

(I)

wherein

R represents phenyl, thienyl or pyridinyl wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;

and wherein pyridinyl is optionally substituted by lower alkoxy, amino or halogen;

X represents a group C=Y, wherein Y stands for oxygen or nitrogen substituted by hydroxy or lower alkoxy;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and pharmaceutically acceptable salts thereof;

or wherein

R represents phenyl or pyridinyl wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, formyl, cyano, halogen, and nitro; and wherein two adjacent substituents are methylenedioxy; and wherein pyridinyl is optionally substituted by lower alkoxy, amino or halogen;

X represents oxygen;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and pharmaceutically acceptable salts thereof;

and wherein the prefix lower denotes a radical having up to and including a maximum of 7, especially up to and including a maximum of 4 carbon atoms.

These compounds are disclosed in WO2004/103994 A1, which is incorporated by cross-reference herein. These compounds have been shown to arrest tumour cell proliferation and induce apoptosis.

The synthesis of compounds of formula I is described in WO2004/103994 A1, in general on pages 29-35, and specifically on pages 39-55, which are incorporated herein by cross-reference. They may be prepared as disclosed or by an analogous method to the processes described therein.

One compound falling within this class, known as BAL27862, and shown in WO2004/103994 A1 as example 58, and specifically incorporated by reference herein, has the structure and chemical name given below:

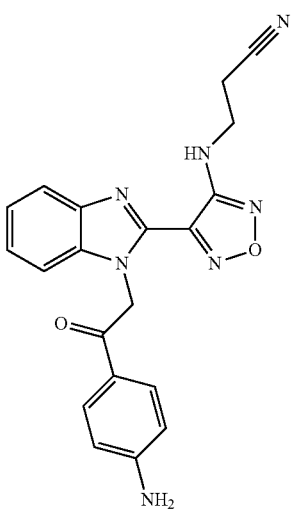 [SMILES: N#CCCNc1nonc1-c1nc2ccccc2n1CC(=O)c1ccc(N)cc1]

Chemical name: 3-(4-{1-[2-(4-Amino-phenyl)-2-oxo-ethyl]-1H-benzoimidazol-2-yl}-furazan-3-ylamino)-propionitrile; or herein as Compound A.

Further compounds exemplified in WO2004/103994 A1 as examples 50 and 79 respectively, and also specifically incorporated by cross-reference herein, have the structures and chemical names given below:

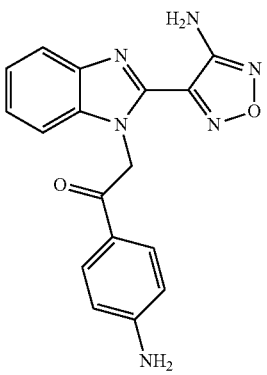 [SMILES: Nc1ccc(C(=O)Cn2c(-c3nonc3N)nc3ccccc32)cc1]

Chemical name: 2-[2-(4-Amino-furazan-3-yl)-benzoimidazol-1-yl]-1-(4-amino-phenyl)-ethanone; or herein as Compound B
and

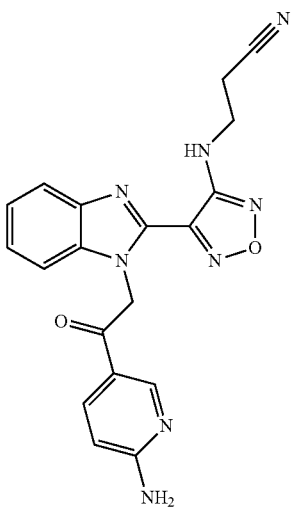 [SMILES: N#CCCNc1nonc1-c1nc2ccccc2n1CC(=O)c1ccc(N)nc1]

Chemical name: 3-(4-{1-[2-(6-Amino-pyridin-3-yl)-2-oxo-ethyl]-1H-benzoimidazol-2-yl}-furazan-3-ylamino)-propionitrile; or herein as Compound C.

BAL27862 has activity across a broad panel of experimental, solid tumour xenograft models. Moreover, activity is retained even against tumour models which are selected for resistance to conventional microtubule targeting agents (including the vinca-alkaloid microtubule destabilisers and the microtubule stabilisers paclitaxel and epothilone B). BAL27862 activity is not affected by over-expression of the P-gp pump in any models tested in vitro, nor in human mammary tumour xenografts. Additionally, BAL27862 retained its activity despite elevated levels of beta-tubulin subtype III and mutations in tubulin subtype I.

Hence, BAL27862 activity is not affected by a number of factors that confer resistance to conventional microtubule targeting agents.

Moreover, it is known that compounds of general formula I have a different effect on the phenotype of cells compared to other microtubule targeting agents, including other microtubule destabilisers. Treatment with a compound of general formula I induces a consistent microtubule phenotype in tumour cell lines derived from a variety of organs, for example lung, cervix and breast, as seen in FIG. 1. Staining the microtubules in these cells with an anti-alpha-tubulin antibody shows that rather than the mitotic spindle fibres of untreated cells, only dot-like structures are visible in the treated cells. This same effect is also shown using Compounds C and B in FIGS. 2A and 2B respectively on the lung cancer cell line A549. It is however very distinct from that observed with the conventional microtubule targeting agents vinblastine, colchicine, paclitaxel and nocodazole as seen in FIGS. 3B, 3C, 3D and 4, respectively. The microtubules were stained with an anti-alpha-tubulin antibody and the cells viewed at a 1000× magnification (FIGS. 3, 4). For the cells treated with BAL27862, multiple dot-like structures are visible, whereas, in stark contrast, the other conventional drugs produce filamentous microtubule structures, or dense microtubule aggregate structures. These differences at the phenotypic level, at compound doses considered optimal in terms of antiproliferative effect, indicate a difference in the mode of action at the molecular level.

Furthermore, it is known that BAL27862 elicits a dominant microtubule phenotype in the presence of the other microtubule targeting agents. Treatment with vinblastine, colchicine, paclitaxel or nocodazole alone induced the microtubule phenotypes characteristic of these agents (FIG. 5A, 5D, 5G, 6C-6F respectively). However, combination treatment with BAL27862 for the last 4 hours resulted in disruption of these phenotypes; despite the continued presence of vinblastine, colchicine, paclitaxel or nocodazole (FIG. 5B, 5E, 5H, 6G-6J respectively). In contrast, treating first with BAL27862 and subsequently for 4 hours in combination with vinblastine, colchicine, paclitaxel or nocodazole had no impact on generation of the phenotype consistent with BAL27862 treatment (FIG. 5C, 5F, 5I, 6K-6N respectively).

These data all demonstrate that BAL27862 affects microtubule biology in a different manner than conventional microtubule targeting agents.

Thus, from information about conventional microtubule targeting agents, predictions cannot be made concerning if, or how, particular genes are involved in the action of compounds of general formula I.

An object of the present invention is to identify factors which are associated with response to compounds of formula I or pharmaceutically acceptable derivatives thereof, for example to identify factors associated with resistance to compounds of general formula I, in particular BAL27862 or pharmaceutically acceptable derivatives thereof, as defined below.

It has surprisingly been found that phospho-Akt may be used as a biomarker of response to treatment with a compound of general formula I or pharmaceutically acceptable derivatives thereof, as defined below.

In one preferred embodiment of the invention, relatively high phospho-Akt levels in a tumour sample are associated with inherent resistance to BAL27862.

To date, the Akt family consists of three known genes, also referred to as isoforms, Akt1, Akt2 and Akt3. These genes are homologous at the nucleic acid level, as well as at the polypeptide sequence level. The Akt genes are also known by a variety of alternative names, reflecting their discovery by different groups. The name Akt arose from its discovery as the human homologue of the proto-oncogene of the transforming retrovirus AKT8. Akt is also known as protein kinase B, or RAC (Related to A and C kinases), since these Akt proteins are closely related to protein kinase A (PKA) and protein kinase C (PKC). Thus, the Akt family is known by the following synonyms c-AKT; proto-oncogene c-Akt; protein kinase B; PKB; RAC; RAC serine/threonine-protein kinase; rac protein kinase and RAC-PK. Akt1, the gene first discovered, is also known as c-AKT1; PKB; PKB-alpha; PRKBA; RAC; RAC-alpha serine/threonine-protein kinase; RAC-ALPHA; RAC-PK-alpha and MGC99656. Akt2 is also known as protein kinase Akt-2; protein kinase B beta; PKBBETA; PRKBB; RAC-BETA; RAC-beta serine/threonine-protein kinase and RAC-PK-beta. Akt3 is also known as PKB-gamma; PKBG; PRKBG; RAC-gamma serine/threonine-protein kinase; RAC-gamma; RAC-PK-gamma; DKFZP434N0250 and STK-2. Alternative splice transcript variants have also been found for some of these genes. Alternative splice transcript variants encoding distinct isoforms have been described for Akt3, namely RAC-gamma serine/threonine-protein kinase isoform 1 and RAC-gamma serine/threonine-protein kinase isoform 2, which differ in length. The designation Akt shall be used herein to encompass the three related proteins Akt1, Akt2, Akt3 and all the synonyms listed above, including isoforms.

Akt may be post-translationally modified, including by phosphorylation at one or more sites. For example Akt1 is known to be able to be phosphorylated on Ser-124, Thr-308, Thr-450, and Ser-473. More than one site may be phosphorylated simultaneously. Regulation of the function of Akt has been particularly identified in connection with the phosphorylation of two sites: a threonine: T308 (Akt 1), T309 (Akt 2), T305 (Akt 3), and a serine: S473 (Akt 1), S474 (Akt 2), S472 (Akt 3).

Phosphoinositide dependent kinase 1 (PDK1) is thought to phosphorylate threonine 308, while mTOR Complex 2 (mTORC2) has recently been identified as PDK2, as it is thought to phosphorylate serine 473 of Akt1.

As used herein, phospho-Akt shall refer to Akt that has been phosphorylated on one or more residues, with the proviso that for Akt1, Akt2, and Akt3 the designation phospho-Akt is used to indicate phosphorylation at a site other than T308, T309 or T305 respectively. To clarify this further, the phospho-Akt may or may not be phosphorylated at T308, T309 or T305 for Akt1, Akt2 and Akt3 respectively, but the designation phospho-Akt indicates phosphorylation at sites other than these. Phospho-Akt may optionally also be post-translationally modified in a way other than by phosphorylation.

More preferably, phospho-Akt shall refer to Akt that has been phosphorylated on the following serine residue:
for Akt1: S473;
for Akt2: S474; and
for Akt3: S472.
This preferred embodiment therefore does not encompass the Akt3 encoded by RAC-gamma serine/threonine-protein kinase isoform 2, since it does not have a serine 472.

Protein sequences coding for human Akt1, Akt2 and Akt3 are available via National Center for Biotechnology Information (NCBI) accession numbers Akt1: NP_005154.2, see SEQ. ID. No. 1 (see also NP_001014431 and NP_001014432), Akt2: NP_001617.1, see SEQ ID No. 2 and Akt3: NP_005456.1: RAC-gamma serine/threonine-protein kinase isoform 1, see SEQ ID No. 3.

One aspect of the present invention relates to use of phospho-Akt as a biomarker for predicting the response to a compound, wherein phospho-Akt is Akt that has been phosphorylated on one or more residues, with the proviso that for Akt1, Akt2, and Akt3 the designation phospho-Akt is used to indicate phosphorylation at a site other than T308, T309 or T305 respectively, wherein the compound is a compound of general formula I,

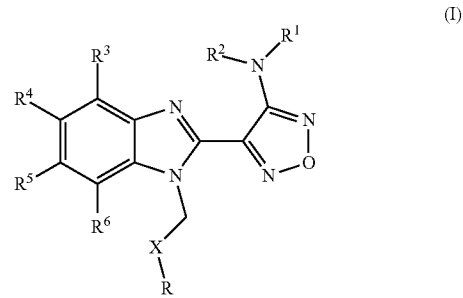

wherein
R represents phenyl, thienyl or pyridinyl
  wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;
and wherein pyridinyl is optionally substituted by lower alkoxy, amino or halogen;
X represents a group C=Y, wherein Y stands for oxygen or nitrogen substituted by hydroxy or lower alkoxy;

R¹ represents hydrogen, lower alkylcarbonyl, hydroxy-lower alkyl or cyano-lower alkyl;

R², R³ and R⁶ represent hydrogen;

R⁴ and R⁵, independently of each other, represent hydrogen, lower alkyl or lower alkoxy;

or R⁴ and R⁵ together represent methylenedioxy;

and pharmaceutically acceptable derivatives thereof, or wherein

R represents phenyl or pyridinyl wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, formyl, cyano, halogen, and nitro; and wherein two adjacent substituents are methylenedioxy; and wherein pyridinyl is optionally substituted by lower alkoxy, amino or halogen;

X represents oxygen;

R¹ represents hydrogen, lower alkylcarbonyl, hydroxy-lower alkyl or cyano-lower alkyl;

R², R³ and R⁶ represent hydrogen;

R⁴ and R⁵, independently of each other, represent hydrogen, lower alkyl or lower alkoxy;

or R⁴ and R⁵ together represent methylenedioxy;

and pharmaceutically acceptable derivatives thereof;

and wherein the prefix lower denotes a radical having up to and including a maximum of 7, especially up to and including a maximum of 4 carbon atoms.

Preferably the response may be of a disease in a subject. Also preferably the response may be to treatment, i.e. to treatment with the compound of general formula I or pharmaceutically acceptable derivatives thereof.

The biomarker phospho-Akt is measured ex vivo in a sample or samples taken from the human or animal body, preferably taken from the human body. The sample or samples are pre-obtained from the human or animal body, preferably pre-obtained from the human body.

In a preferred embodiment, the invention relates to use of phospho-Akt as a biomarker for predicting the resistance of a disease in a subject to a compound of general formula I or pharmaceutically acceptable derivatives thereof as defined above.

Preferably the pharmaceutically acceptable derivative is selected from the group consisting of a salt, solvate, pro-drug, salt of a pro-drug, polymorph and isomer of a compound of general formula I. Pro-drugs are preferably ester and amides of naturally occurring amino acids, small peptides or pegylated hydroxy acids. More preferably, the pro-drug is an amide formed from an amino group present within the R group of the compound of general formula I and the carboxy group of glycine, alanine or lysine.

Particularly preferably the compound is

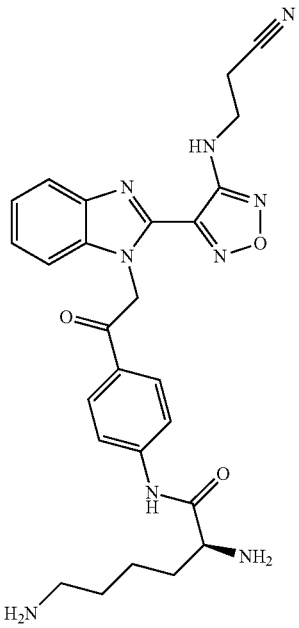 [SMILES: N#CCCNc1nonc1-c1nc2ccccc2n1CC(=O)c1ccc(NC(=O)[C@@H](N)CCCCN)cc1]

or a pharmaceutically acceptable salt thereof, preferably a hydrochloride salt thereof, most preferably a dihydrochloride salt thereof.

Another aspect of the present invention relates to a method for predicting the response of a disease in a subject to a compound of general formula I or pharmaceutically acceptable derivatives thereof as defined above, comprising the steps of:

a) measuring a level of phospho-Akt as defined above in a sample pre-obtained from the subject to obtain a value or values representing this level; and b) comparing the value or values from step a) to a standard value or set of standard values.

Further preferably the response which is predicted is resistance.

The measuring of a level or levels of phospho-Akt is performed ex-vivo in a sample pre-obtained from the subject. Pre-obtained refers to the fact that the sample is obtained before it is subjected to any method involving measuring the level of the biomarker, and pre-obtained is not to be understood as in relation to treatment.

In a preferred embodiment, a higher level of phospho-Akt in the sample from the subject relative to the standard value or set of standard values predicts resistance.

Also preferably, the disease is a neoplastic or autoimmune disease. More preferably the disease is cancer. Especially preferably the cancer is selected from the group consisting of breast cancer, prostate cancer, cervical cancer, gastric cancer, ovarian cancer, colorectal cancer (i.e including colon cancer and rectal cancer), pancreatic cancer, liver cancer, brain cancer, neuroendocrine cancer, lung cancer, kidney cancer, hematological malignancies, melanoma and sarcomas. More especially preferably the cancer is selected from the group consisting of breast cancer, cervical cancer, gastric cancer, lung cancer, colorectal cancer and melanoma. Particularly preferably the cancer is selected from the group consisting of gastric cancer, lung cancer, colorectal cancer and melanoma.

In a further aspect, the invention relates to a method of treating a neoplastic or autoimmune disease, preferably cancer, in a subject in need thereof, comprising measuring a level of phospho-Akt as defined above in a sample from the subject to obtain a value or values representing this level, and treating the subject with a compound of general formula I or a pharmaceutically acceptable derivative thereof as defined above, if the level of phospho-Akt in said sample is not higher than a standard value or set of standard values.

In yet a further aspect, the invention relates to phospho-Akt as defined above for use in the treatment of a neoplastic or autoimmune disease, preferably cancer, comprising measuring a level of phospho-Akt in a sample from a subject to obtain a value or values representing this level, and treating the subject with a compound of general formula I or a pharmaceutically acceptable derivative thereof as defined above, if the level of phospho-Akt is not higher than a standard value or set of standard values.

The measuring of a level of phospho-Akt is performed ex-vivo in a sample pre-obtained from the subject.

The invention also relates in another aspect to a method of treating a neoplastic or autoimmune disease, preferably cancer, by first decreasing a level of phospho-Akt as defined above in a subject that has a sample with a higher level of phospho-Akt compared to a standard level or set of standard levels, then treating the subject with a compound of general formula I or a pharmaceutically acceptable derivative thereof as defined above.

In yet another aspect the invention relates to a kit for predicting the response to a compound of general formula I or a pharmaceutically acceptable derivative thereof, as defined above, comprising reagents necessary for measuring the level of phospho-Akt as defined above in a sample. More preferably the kit also comprises a comparator module which comprises a standard value or set of standard values to which the level of phospho-Akt in the sample is compared.

More preferably the kit comprises a compound of general formula I or a pharmaceutically acceptable derivative thereof as defined above. In an especially preferred embodiment the kit comprises a compound of the following formula or a pharmaceutically acceptable salt thereof

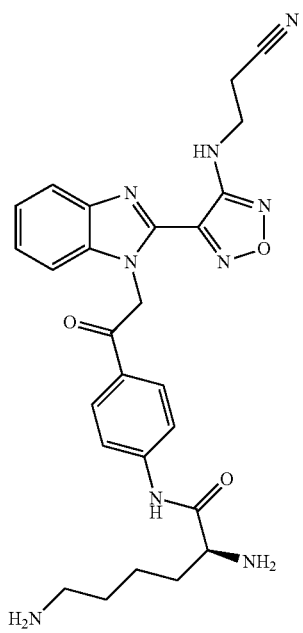

Chemical name: S-2,6-Diamino-hexanoic acid [4-(2-{2-[4-(2-cyano-ethylamino)-furazan-3-yl]-benzoimidazol-1-yl}-acetyl)-phenyl]-amide In a particularly preferred embodiment the pharmaceutically acceptable salt is a dihydrochloride salt.

Another further aspect of the invention relates to a device for predicting the response to a compound of general formula I or a pharmaceutically acceptable derivative thereof as defined above, comprising reagents necessary for measuring a level of phospho-Akt as defined above in a sample and a comparator module which comprises a standard value or set of standard values to which the level of phospho-Akt in the sample is compared.

In a preferred embodiment, the reagents in the kit or device comprise a capture reagent comprising a detector for phospho-Akt, and a detector reagent. Especially preferably the capture reagent is an antibody. Also preferably, the disease is predicted to be resistant to treatment with said compound when phospho-Akt is higher relative to a standard value or set of standard values. In a preferred embodiment, the comparator module is included in instructions for use of the kit. In another preferred embodiment the comparator module is in the form of a display device.

Embodiments of the present invention will now be described by way of example with reference to the accompanying figures. The invention however is not to be understood as limited to these embodiments.

BRIEF DESCRIPTION OF THE FIGURES

FIGS. 1A and 1B: A549 NSCLC cells;
FIGS. 1C and 1D: HeLa cervical cancer cells;
FIGS. 1E and 1F: SKBR3 breast cancer cells
Vehicle control treatment:
FIGS. 1A, 1C & 1E,
BAL27862 treatment:
FIGS. 1B, 1D & 1F.
FIG. 2A: treatment with 20 nM compound C
FIG. 2B: treatment with 80 nM compound B

FIG. 5A: 24 hours vinblastine treatment;

FIG. 5B: 24 hours vinblastine treatment with the final 4 hours including BAL27862;

FIG. 5C: 24 hours BAL27862 treatment with the final 4 hours including vinblastine.

FIG. 5D: 24 hours colchicine treatment;

FIG. 5E: 24 hours colchicine treatment with the final 4 hours including BAL27862;

FIG. 5F: 24 hours BAL27862 treatment with the final 4 hours including colchicine.

FIG. 5G: 24 hours paclitaxel treatment;

FIG. 5H: 24 hours paclitaxel treatment with the final 4 hours including BAL27862;

FIG. 5I: 24 hours BAL27862 treatment with the final 4 hours including paclitaxel.

FIG. 6A: 24 hours control treatment;

FIG. 6B: 24 hours of 25 nM BAL27862 treatment;

FIG. 6C: 24 hours of 50 nM nocodazole treatment

FIG. 6D: 24 hours of 100 nM nocodazole treatment

FIG. 6E: 24 hours of 150 nM nocodazole treatment

FIG. 6F: 24 hours of 200 nM nocodazole treatment

FIG. 6G: 24 hours of 50 nM nocodazole treatment with the final 4 hours including 25 nM BAL27862;

FIG. 6H: 24 hours of 100 nM nocodazole treatment with the final 4 hours including 25 nM BAL27862;

FIG. 6I: 24 hours of 150 nM nocodazole treatment with the final 4 hours including 25 nM BAL27862;

FIG. 6J: 24 hours of 200 nM nocodazole treatment with the final 4 hours including 25 nM BAL27862;

FIG. 6K: 24 hours of 25 nM BAL27862 treatment with the final 4 hours including 50 nM nocodazole;

FIG. 6L: 24 hours of 25 nM BAL27862 treatment with the final 4 hours including 100 nM nocodazole;

FIG. 6M: 24 hours of 25 nM BAL27862 treatment with the final 4 hours including 150 nM nocodazole;

FIG. 6N: 24 hours of 25 nM BAL27862 treatment with the final 4 hours including 200 nM nocodazole.

FIG. 9: shows the protein sequence of Akt1 (RAC-alpha serine/threonine-protein kinase) [*Homo sapiens*] (SEQ. ID. No. 1)

FIG. 10: shows the protein sequence of Akt2 (RAC-beta serine/threonine-protein kinase) [*Homo sapiens*] (SEQ. ID. No. 2)

FIG. 11: shows the protein acid sequence of Akt3 (RAC-gamma serine/threonine-protein kinase isoform 1) [*Homo sapiens*] (SEQ. ID. No. 3)

DETAILED DESCRIPTION

Compounds of Formula I

Figure 1:
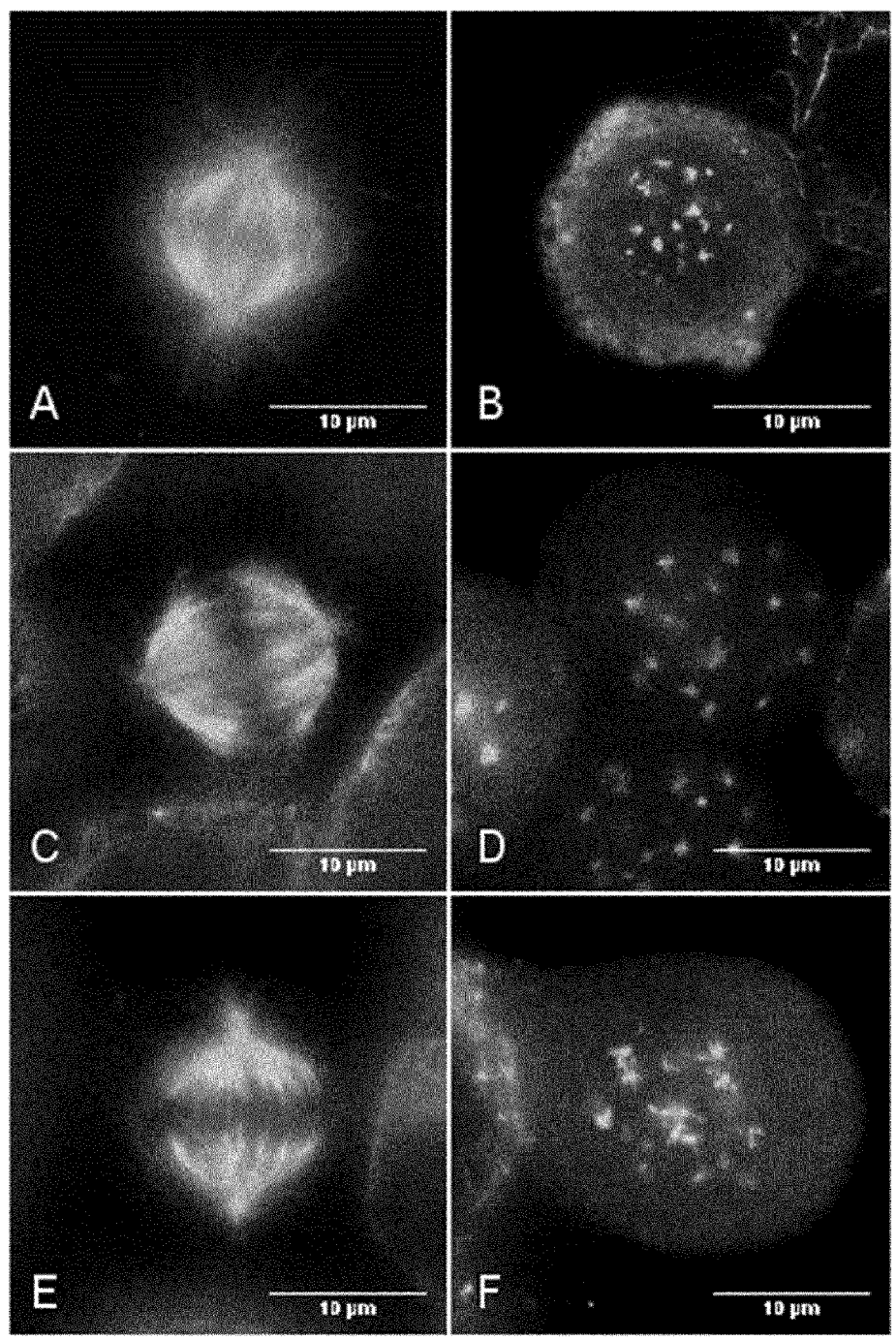
FIG. 1: Shows the treatment of human tumour cell lines from different histotypes with 50 nM BAL27862. The microtubules of mitotic or G2/M arrested cells were stained after 24 hours treatment with 50 nM BAL27862 or vehicle control.

The compounds according to the invention are represented by general formula I:

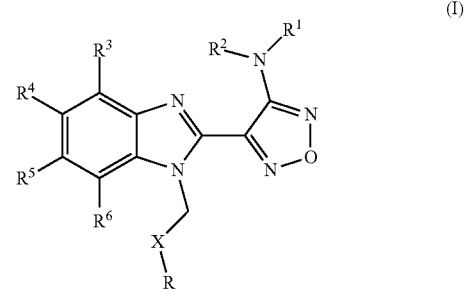

(I)

wherein

R represents phenyl, thienyl or pyridinyl
wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;
and wherein pyridinyl is optionally substituted by lower alkoxy, amino or halogen;

X represents a group C=Y, wherein Y stands for oxygen or nitrogen substituted by hydroxy or lower alkoxy;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and pharmaceutically acceptable derivatives thereof, or wherein

R represents phenyl or pyridinyl
wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, formyl, cyano, halogen, and nitro; and wherein two adjacent substituents are methylenedioxy; and wherein pyridinyl is optionally substituted by lower alkoxy, amino or halogen;

X represents oxygen;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and pharmaceutically acceptable derivatives thereof;

and wherein the prefix lower denotes a radical having up to and including a maximum of 7, especially up to and including a maximum of 4 carbon atoms.

Heterocyclyl designates preferably a saturated, partially saturated or unsaturated, mono- or bicyclic ring containing 4-10 atoms comprising one, two or three heteroatoms selected from nitrogen, oxygen and sulfur, which may, unless otherwise specified, be carbon or nitrogen linked, wherein a ring nitrogen atom may optionally be substituted by a group selected from lower alkyl, amino-lower alkyl, aryl, aryl-lower alkyl and acyl, and a ring carbon atom may be substituted by lower alkyl, amino-lower alkyl, aryl, aryl-lower alkyl, heteroaryl, lower alkoxy, hydroxy or oxo. Examples of heterocyclyl are pyrrolidinyl, oxazolidinyl, thiazolidinyl, piperidinyl, morpholinyl, piperazinyl, dioxolanyl and tetrahydropyranyl.

Acyl designates, for example, alkylcarbonyl, cyclohexylcarbonyl, arylcarbonyl, aryl-lower alkylcarbonyl, or heteroarylcarbonyl. Lower acyl is preferably lower alkylcarbonyl, in particular propionyl or acetyl.

Preferably, the compound of general formula I according to the invention is defined as wherein $R^1$ is selected from the group consisting of hydrogen, acetyl, $CH_2CH_2CN$ and $CH_2CH_2CH_2OH$.

In one preferred embodiment, the compound of general formula I according to the invention is selected from the group consisting of:

4-(1-Phenacyl-1H-benzimidazol-2-yl)-furazan-3-ylamine,

4-[1-(4-Bromophenacyl)-1H-benzimidazol-2-yl]-furazan-3-ylamine oxime,

N-{4-[1-(4-Chlorophenacyl)-1H-benzimidazol-2-yl]-furazan-3-yl}-acetamide,

4-[1-(4-Chlorophenacyl)-1H-benzimidazol-2-yl]-furazan-3-yl-N-(2-cyanoethyl)-amine, 4-[1-(4-Chlorophenacyl)-1H-benzimidazol-2-yl]-furazan-3-yl-N-(3-hydroxypropyl)-amine, 4-[1-(3-Amino-4-chlorophenacyl)-1H-benzimidazol-2-yl]-furazan-3-ylamine, 4-[1-(3-Methoxy-4-methoxymethoxy-phenacyl)-1H-benzimidazol-2-yl]-furazan-3-ylamine, and pharmaceutically acceptable derivatives thereof.

In another preferred embodiment, the compound of general formula I according to the invention is:

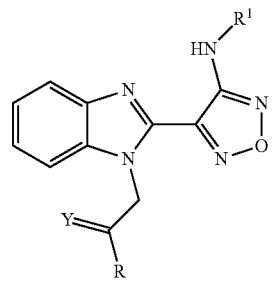

wherein

R, Y and $R^1$ are defined as follows:

| R | Y | $R^1$ |
|---|---|---|
| 4-Cl-phenyl | O | H |
| phenyl | NOH | H |
| phenyl | NOMe | H |
| 4-MeO-phenyl | O | H |
| 4-MeO-phenyl | NOH | H |
| 4-Cl-phenyl | NOH | H |
| 4-Cl-phenyl | NOMe | H |
| 3-MeO-phenyl | O | H |
| 3-MeO-phenyl | NOH | H |

| R | Y | R¹ |
|---|---|---|
| 3-MeO-C₆H₄- | NOMe | H |
| 4-Ph-C₆H₄- | O | H |
| 4-Ph-C₆H₄- | NOH | H |
| 4-Ph-C₆H₄- | NOMe | H |
| 4-Br-C₆H₄- | O | H |
| 4-Br-C₆H₄- | NOMe | H |
| 2,4-Cl₂-C₆H₃- | O | H |
| 2-Cl-C₆H₄- | O | H |
| 2-Cl-C₆H₄- | NOH | H |
| 2-Cl-C₆H₄- | NOMe | H |
| 3-Cl-C₆H₄- | O | H |
| 3-Cl-C₆H₄- | NOH | H |
| 3-Cl-C₆H₄- | NOMe | H |
| 4-MeO-C₆H₄- | NOMe | H |
| 4-Et₂N-C₆H₄- | O | H |
| C₆H₅- | O | Ac |
| 4-F₃C-C₆H₄- | O | H |
| 4-Me-C₆H₄- | O | H |
| 3,4-methylenedioxy-C₆H₃- | O | H |
| 4-Br-C₆H₄- | O | CH₂CH₂CN |
| 4-MeO-C₆H₄- | O | CH₂CH₂CN |
| 4-O₂N-C₆H₄- | O | H |
| 4-H₂N-C₆H₄- | O | H |
| 3,4-Me₂-C₆H₃- | O | CH₂CH₂CH₂OH |
| 3,4-Me₂-C₆H₃- | O | H |
| 3,4-Me₂-C₆H₃- | O | CH₂CH₂CN |

| R | Y | R¹ |
|---|---|---|
| 4-Et-C6H4- | O | H |
| 4-Et-C6H4- | O | CH2CH2CN |
| 4-O2N-C6H4- | O | CH2CH2CN |
| 4-H2N-C6H4- | O | CH2CH2CN |
| pyridin-2-yl | O | H |
| 4-AcNH-C6H4- | O | H |
| 4-NC-C6H4- | O | H |
| 4-Me-2-O2N-3-AcNH-C6H3- | O | H |
| 4-Me-2-O2N-3-H2N-C6H3- | O | H |
| 3-O2N-4-Cl-C6H3- | O | H |
| 4-F-C6H4- | O | H |
| 3-O2N-4-MeO-C6H3- | O | H |
| 3-H2N-4-MeO-C6H3- | O | CH2CH2CN |

| R | Y | R¹ |
|---|---|---|
| 6-Cl-pyridin-3-yl | O | H |
| 2,5-diF-C6H3- | O | H |
| thiophen-2-yl | O | H |
| 3-MeO-4-BnO-C6H3- | O | H |
| 3-MeO-4-HO-C6H3- | O | H |
| 3-MeO-4-AcO-C6H3- | O | H |
| 3,4-diMeO-C6H3- | O | H |
| 4-(2-methoxyethoxy)-C6H4- | O | H |
| 6-H2N-pyridin-3-yl | O | H |
| 6-H2N-pyridin-3-yl | O | CH2CH2CN |
| 3,4-diHO-C6H3- | O | H |
| 3,4-bis(MOMO)-C6H3- | O | H |
| 6-MeO-pyridin-3-yl | O | CH2CH2CN | or pharmaceutically acceptable derivatives thereof.

In yet another preferred embodiment, the compound of general formula I according to the invention is selected from the group consisting of:
4-(1-Phenoxymethyl-1H-benzimidazol-2-yl)-furazan-3-ylamine,
4-[1-(4-Fluorophenoxymethyl)-1H-benzimidazol-2-yl]-furazan-3-ylamine,
4-[1-(3,4-Dimethylphenoxymethyl)-1H-benzimidazol-2-yl]-furazan-3-yl-N-(2-cyanoethyl)-amine,
and compounds represented by the formula:

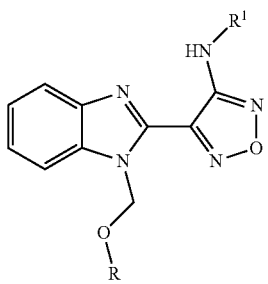

wherein R and R¹ are as defined below

| R | R¹ |
|---|---|
| 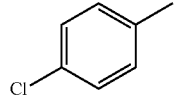 | H |
| 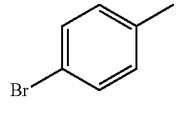 | H |
| 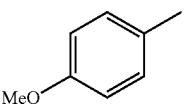 | H |
| 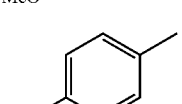 | H |
| 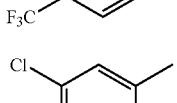 | H |
| 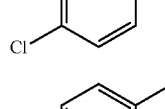 | CH₂CH₂CN |
| 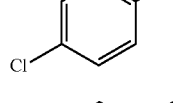 | CH₂CH₂CN |
|  | CH₂CH₂CN |
| 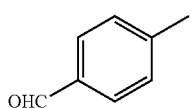 | H |
| 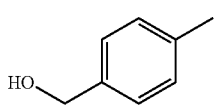 | H |
| 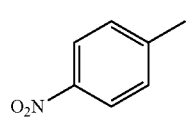 | H |
| 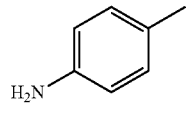 | H |
| 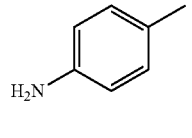 | H |
| 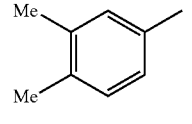 | H |
| 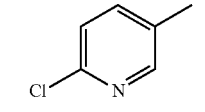 | CH₂CH₂CN |

-continued

| R | R¹ |
|---|---|
| 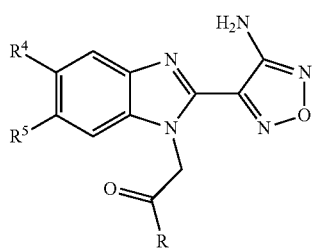 (H₂N-pyridine with methyl) | H | or pharmaceutically acceptable derivatives thereof.

In still yet another preferred embodiment the compound of general formula I according to the invention is:

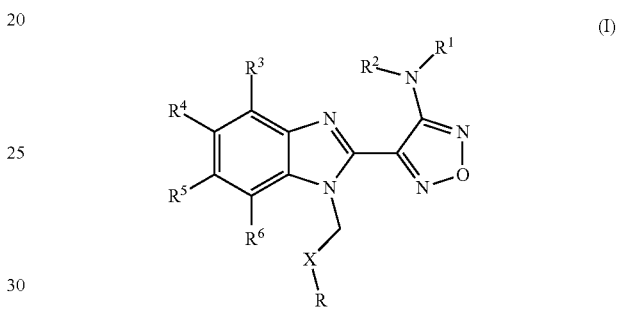

wherein R, R⁴ and R⁵ are as defined below

| R | R⁴ | R⁵ |
|---|---|---|
| phenyl | Me | Me |
| 4-Br-phenyl | Me | Me |
| 4-Cl-phenyl | Me | Me |
| 4-MeO-phenyl | Me | Me |
| 4-Ph-phenyl | Me | Me |
| phenyl | OMe | OMe |
| 4-Cl-phenyl | OMe | OMe |
| 4-Br-phenyl | OMe | OMe |
| 4-MeO-phenyl | OMe | OMe |
| 4-Ph-phenyl | OMe | OMe | or pharmaceutically acceptable derivatives thereof.

More preferably, the compound according to the invention is a compound of general formula I $$\text{(I)}$$

wherein

R represents phenyl or pyridinyl
wherein phenyl is optionally substituted by one or two substituents independently selected from lower alkyl, lower alkoxy, amino, acetylamino, halogen and nitro; and wherein pyridinyl is optionally substituted by amino or halogen;

X represents a group C=O;

R¹ represents hydrogen or cyano-lower alkyl;

R², R³, R⁴, R⁵ and R⁶ represent hydrogen;

and pharmaceutically acceptable derivatives thereof, and wherein the prefix lower denotes a radical having up to and including a maximum of 7, especially up to and including a maximum of 4 carbon atoms.

Especially preferably, the compound according to the invention is represented by the following formula

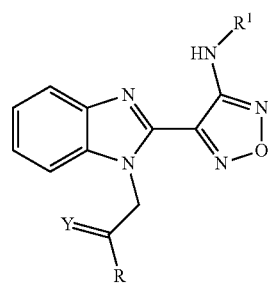

wherein R, Y and R¹ are defined as follows:

| R | Y | R¹ |
|---|---|---|
| H₂N–C₆H₄–(4-methyl) | O | H |
| H₂N–C₆H₄–(4-methyl) | O | CH₂CH₂CN |
| H₂N–pyridyl–(5-methyl) | O | H |
| H₂N–pyridyl–(5-methyl) | O | CH₂CH₂CN | or pharmaceutically acceptable derivatives thereof.

More especially preferably, the compound according to the invention is represented by the following formula

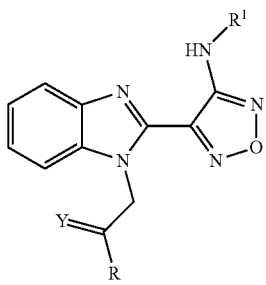

wherein R, Y and R1 are defined as follows:

| R | Y | R1 |
|---|---|---|
| H₂N–C₆H₄–(4-methyl) | O | CH₂CH₂CN |
| H₂N–C₆H₄–(4-methyl) | O | H |
| H₂N–pyridyl–(5-methyl) | O | CH₂CH₂CN | or pharmaceutically acceptable derivatives thereof.

Particularly preferably, the compound of general formula I according to the invention is

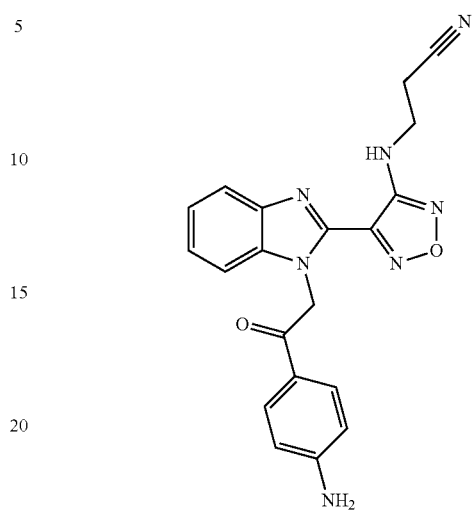

or pharmaceutically acceptable derivatives thereof.

The term derivative or derivatives in the phrase "pharmaceutically acceptable derivative" or "pharmaceutically acceptable derivatives" of compounds of general formula I relates to salts, solvates and complexes thereof and to solvates and complexes of salts thereof, as well as to pro-drugs, polymorphs, and isomers thereof (including optical, geometric and tautomeric isomers) and also salts of pro-drugs thereof. In a more preferred embodiment, it relates to salts and pro-drugs, as well as to salts of pro-drugs thereof.

Salts are preferably acid addition salts. Salts are formed, preferably with organic or inorganic acids, from compounds of formula (I) with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethanesulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

The compound according to the invention may be administered in the form of a pro-drug which is broken down in the human or animal body to give a compound of the formula I. Examples of pro-drugs include in vivo hydrolysable esters and amides of a compound of the formula I. Particular pro-drugs considered are ester and amides of naturally occurring amino acids and ester or amides of small peptides, in particular small peptides consisting of up to five, preferably two or three amino acids, as well as esters and amides of pegylated hydroxy acids, preferably hydroxy acetic acid and lactic acid. Pro-drug esters are formed from the acid function of the amino acid or the C terminal of the peptide and suitable hydroxy group(s) in the compound of formula I. Pro-drug amides are formed from the amino function of the amino acid or the N terminal of the peptide and suitable carboxy group(s) in the compound of formula I, or from the acid function of the amino acid or the C terminal of the peptide and suitable amino group(s) in the compound of formula I. Particularly preferably the pro-drug amides are formed from the amino group(s) present within the R group of formula I.

More preferably, the pro-drug is formed by the addition of glycine, alanine or lysine to the compound of formula I.

Even more preferably the compound of general formula I is in the form of a pro-drug selected from the compounds of formulae:

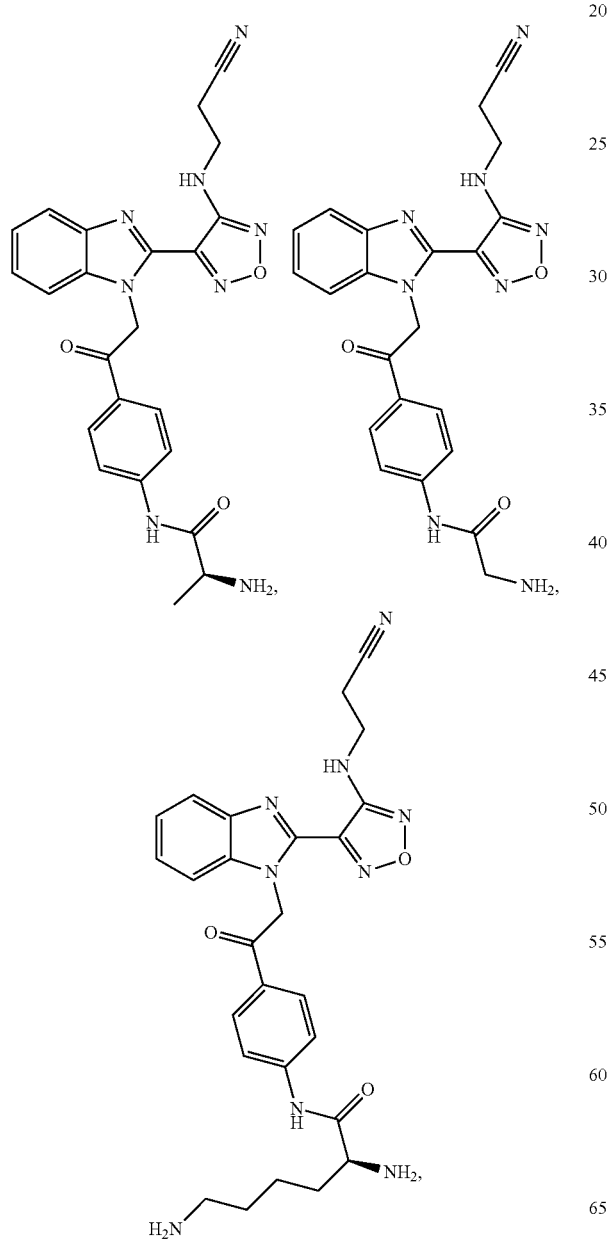

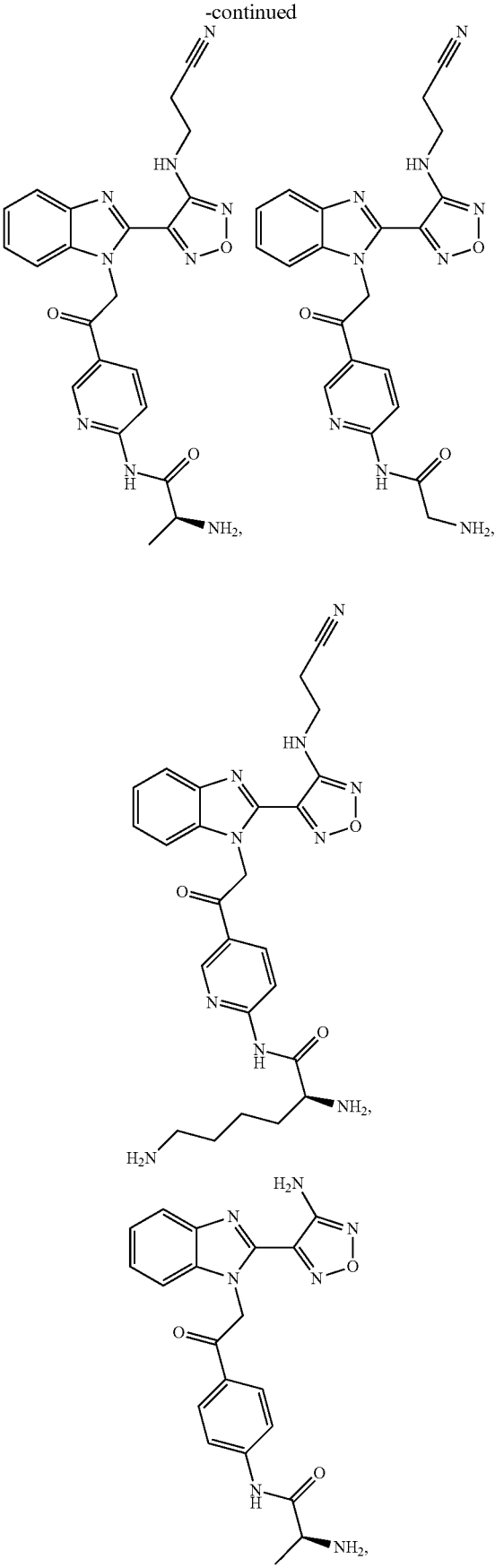

-continued

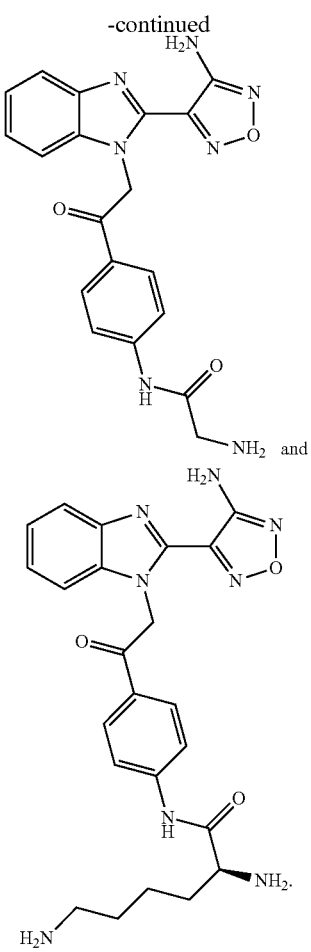

and

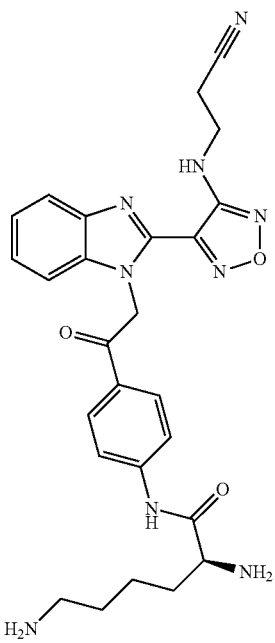 [SMILES: N#CCCNc1nonc1-c1nc2ccccc2n1CC(=O)c1ccc(NC(=O)[C@@H](N)CCCCN)cc1]

In an especially preferred embodiment the compound according to the invention is in the form of a pro-drug which has the following formula

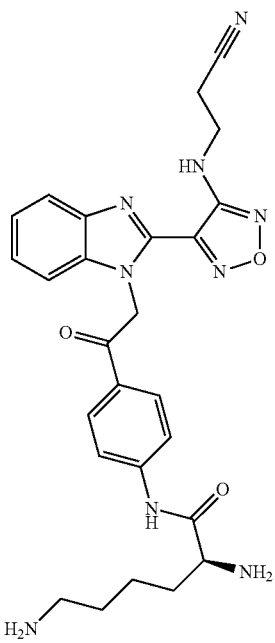 [SMILES: N#CCCNc1nonc1-c1nc2ccccc2n1CC(=O)c1ccc(NC(=O)[C@@H](N)CCCCN)cc1]

In a most especially preferred embodiment the compound according to the invention is a pharmaceutically acceptable salt, preferably a hydrochloride salt thereof, most preferably a dihydrochloride salt thereof, of a compound of the following formula

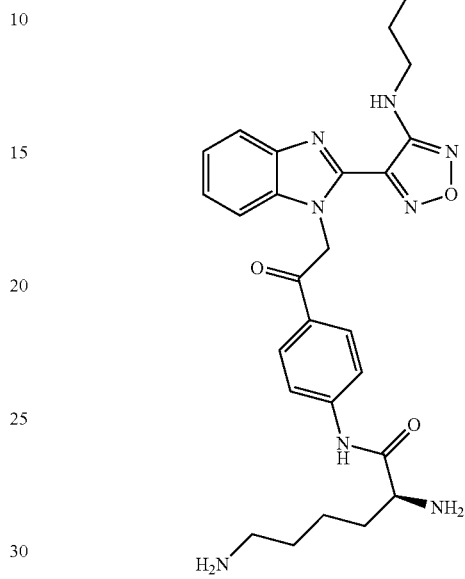

The pharmaceutically active metabolite in vivo in this case is BAL27862.

These pro-drugs may be prepared by processes that are known per se, in particular, a process, wherein a compound of formula (II)

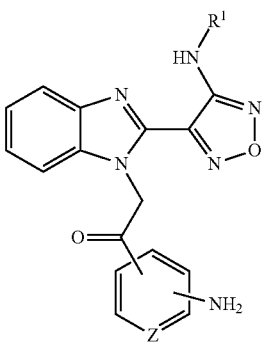

(II)

wherein $R^1$ is defined as for formula (I) and Z is CH or N, or a derivative of such a compound comprising functional groups in protected form,
or a salt thereof is
(1) acylated with an amino acid of formula (III)

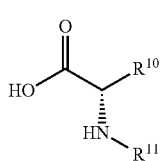

(III)

wherein
R¹⁰ is selected from hydrogen (Gly); methyl (Ala) and protected aminobutyl (Lys) and
R¹¹ is a suitable amino protecting group, and
(2) any protecting groups in a protected derivative of the resulting compound are removed to yield a pro-drug as shown above, and, if so desired,
(3) said pro-drug is converted into a salt by treatment with an acid, or a salt of a compound of formula (II) is converted into the corresponding free compound of formula (II) or into another salt, and/or a mixture of isomeric product compounds is separated into the individual isomers.

Acylation of a compound of formula (II) with an amino acid of formula (III) is performed in a manner known per se, usually in the presence of a suitable polar or dipolar aprotic solvent, with cooling or heating as required, for example in a temperature range from approximately minus 80° C. to approximately plus 150° C., more preferably from minus 30° C. to plus 120° C., especially in a range from approximately around 0° C. to the reflux temperature of the used solvent. Optionally a suitable base is added, in particularly an aromatic base like pyridine or collidine or a tertiary amine base such as triethylamine or diisopropylethylamine, or an inorganic basic salt, e.g. potassium or sodium carbonate.

Acylation may be accomplished under conditions used for amide formation known per se in peptide chemistry, e.g. with activating agents for the carboxy group, such as carbodiimides like N,N'-diethyl-, N,N'-dipropyl-, N,N'-diisopropyl-, N,N'-dicyclohexylcarbodiimide and N-(3-dimethylaminoisopropyl)-N'-ethylcarbodiimide-hydrochloride (EDC), or with agents such as 1-hydroxybenzotriazole (HOBt), benzotriazol-1-yloxytris(dimethylamino)-phosphonium hexafluorophosphate (BOP), O-(7-aza-benzotriazol-1-yl)-N,N,N',N'-tetramethyl-uronium hexafluorophosphate (HATU), 2-(2-oxo-1-(2H)-pyridyl)-1,1,3,3-tetramethyluronium tetrafluoroborate (TPTU), optionally in the presence of suitable bases, catalysts or co-reagents. The carboxy group may also be activated as acyl halogenide, preferably as acyl chloride, e.g. by reaction with thionylchloride or oxalylchloride, or as symmetrical or unsymmetrical anhydride, e.g. by reaction with halogeno formates like ethyl chloroformate, optionally in the presence of suitable bases, catalysts or co-reagents.

If one or more other functional groups, for example carboxy, hydroxy or amino, are or need to be protected in a compound of formula (II) or (III), because they should not take part in the reaction, these are such protecting groups as are usually applied in the synthesis of amides like, in particular peptide compounds, cephalosporins, penicillins, nucleic acid derivatives and sugars, which are known to the skilled persons. Suitable protecting groups for amino groups are for example t-butyl carbamate, benzyl carbamate or 9-fluorenylmethyl carbamate.

The protecting groups may already be present in precursors and should protect the functional groups concerned against unwanted secondary reactions, such as alkylations, acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference books for peptide synthesis and in special books on protective groups such as
J. F. W. McOmie, "Protective Groups in Organic Chemistry", Plenum Press, London and New York 1973, in "Methoden der organischen Chemie" (Methods of organic chemistry), Houben-Weyl, 4th edition, Volume 15/I, Georg Thieme Verlag, Stuttgart 1974, and in T. W. Greene, G. M. Wuts "Protective Groups in Organic Synthesis", Wiley, New York, 2006.

Disease

The compounds of general formula I according to the invention have been shown to arrest cell proliferation and induce cell death, for example by apoptosis.

Deregulation of cell proliferation, or lack of appropriate cell death, has wide ranging clinical implications. A number of diseases associated with such deregulation involve hyperproliferation, inflammation, tissue remodeling and repair. Familiar indications in this category include cancers, restenosis, neointimal hyperplasia, angiogenesis, endometriosis, lymphoproliferative disorders, transplantation related pathologies (graft rejection), polyposis, loss of neural function in the case of tissue remodeling and the like.

Cancer is associated with abnormal cell proliferation and cell death rates. As apoptosis is inhibited or delayed in most types of proliferative, neoplastic diseases, induction of apoptosis is an option for treatment of cancer, especially in cancer types which show resistance to classic chemotherapy, radiation and immunotherapy (Apoptosis and Cancer Chemotherapy, Hickman and Dive, eds., Blackwell Publishing, 1999). Also in autoimmune and transplantation related diseases and pathologies compounds inducing apoptosis may be used to restore normal cell death processes and therefore can eradicate the symptoms and might cure the diseases. Further applications of compounds inducing apoptosis may be in restenosis, i.e. accumulation of vascular smooth muscle cells in the walls of arteries, and in persistent infections caused by a failure to eradicate bacteria- and virus-infected cells. Furthermore, apoptosis can be induced or reestablished in epithelial cells, in endothelial cells, in muscle cells, and in others which have lost contact with extracellular matrix.

A compound according to general formula I or pharmaceutically acceptable derivatives thereof may be used for the prophylactic or especially therapeutic treatment of the human or animal body, in particular for treating a neoplastic disease, autoimmune disease, transplantation related pathology and/or degenerative disease. Examples of such neoplastic diseases include, but are not limited to, epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and glomus tumours, naevi and melanomas, soft tissue tumours and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumours, lymphatic vessel tumours, osseous and chondromatous neoplasms, giant cell tumours, miscellaneous bone tumours, odontogenic tumours, gliomas, neuroepitheliomatous neoplasms, meningiomas, nerve sheath tumours, granular cell tumours and alveolar soft part sarcomas, Hodgkin's and non-Hodgkin's lymphomas, other lymphoreticular neoplasms, plasma cell tumours, mast cell tumours, immunoproliferative diseases, leukemias, miscellaneous myeloproliferative disorders, lymphoproliferative disorders and myelodysplastic syndromes.

The compounds of general formula I or pharmaceutically acceptable derivatives thereof may be used to treat autoimmune diseases. Examples of such autoimmune diseases include, but are not limited to, systemic, discoid or subacute cutaneous lupus erythematosus, rheumatoid arthritis, antiphospholipid syndrome, CREST, progressive systemic sclerosis, mixed connective tissue disease (Sharp syndrome), Reiter's syndrome, juvenile arthritis, cold agglutinin disease, essential mixed cryoglobulinemia, rheumatic fever, ankylosing spondylitis, chronic polyarthritis, myasthenia gravis, multiple sclerosis, chronic inflammatory demyelinating polyneuropathy, Guillan-Barre syndrome, dermatomyositis/polymyositis, autoimmune hemolytic anemia, thrombocytopenic purpura, neutropenia, type I diabetes mellitus, thyroiditis (including Hashimoto's and Grave' disease), Addison's disease, polyglandular syndrome, pemphigus (vulgaris, foliaceus, sebaceous and vegetans), bullous and cicatricial pemphigoid, pemphigoid gestationis, epidermolysis bullosa acquisita, linear IgA disease, lichen sclerosus et atrophicus, morbus Duhring, psoriasis vulgaris, guttate, generalized pustular and localized pustular psoriasis, vitiligo, alopecia greata, primary biliary cirrhosis, autoimmune hepatitis, all forms of glomerulonephritis, pulmonal hemorrhage (goodpasture syndrome), IgA nephropathy, pernicious anemia and autoimmune gastritis, inflammatory bowel diseases (including colitis ulcerosa and morbus Crohn), Behcet's disease, Celic-Sprue disease, autoimmune uveitis, autoimmune myocarditis, granulomatous orchitis, aspermatogenesis without orchitis, idiopatic and secondary pulmonary fibrosis, inflammatory diseases with a possibility of autoimmune pathogenesis, such as pyoderma gangrensosum, lichen ruber, sarcoidosis (including Lofgren and cutaneous/subcutaneous type), granuloma anulare, allergic type I and type IV immunolgical reaction, asthma bronchiale, pollinosis, atopic, contact and airborne dermatitis, large vessel vasculitis (giant cell and Takayasu's arteritis), medium sized vessel vasculitis (polyarteritis nodosa, Kawasaki disease), small vessel vasculitis (Wegener's granulomatosis, Churg Strauss syndrome, microscopic polangiitis, HenochSchoenlein purpura, essential cryoglobulinemic vasculitis, cutaneous leukoklastic angiitis), hypersensitivity syndromes, toxic epidermal necrolysis (Stevens-Johnson syndrome, erythema multiforme), diseases due to drug side effects, all forms of cutaneous, organ-specific and systemic effects due to type I-vu (Coombs classification) immunologic forms of reaction, transplantation related pathologies, such as acute and chronic graft versus host and host versus graft disease, involving all organs (skin, heart, kidney, bone marrow, eye, liver, spleen, lung, muscle, central and peripheral nerve system, connective tissue, bone, blood and lymphatic vessel, genito-urinary system, ear, cartilage, primary and secondary lymphatic system including bone marrow, lymph node, thymus, gastrointestinal tract, including oropharynx, esophagus, stomach, small intestine, colon, and rectum, including parts of above mentioned organs down to single cell level and substructures, e.g. stem cells).

Particularly preferably, the disease according to the invention is a neoplastic or autoimmune disease. In an especially preferred embodiment the disease is cancer.

Examples of cancers in terms of the organs and parts of the body affected include, but are not limited to, the breast, cervix, ovaries, colon, rectum, (including colon and rectum i.e. colorectal cancer), lung, (including small cell lung cancer, non-small cell lung cancer, large cell lung cancer and mesothelioma), endocrine system, bone, adrenal gland, thymus, liver, stomach, intestine, (including gastric cancer), pancreas, bone marrow, hematological malignancies, (such as lymphoma, leukemia, myeloma or lymphoid malignancies), bladder, urinary tract, kidneys, skin, thyroid, brain, head, neck, prostate and testis. Preferably the cancer is selected from the group consisting of breast cancer, prostate cancer, cervical cancer, ovarian cancer, gastric cancer, colorectal cancer, pancreatic cancer, liver cancer, brain cancer, neuroendocrine cancer, lung cancer, kidney cancer, hematological malignancies, melanoma and sarcomas. Especially preferably the cancer is selected from the group consisting of breast cancer, cervical cancer, gastric cancer, lung cancer, colorectal cancer and melanoma. More especially preferably the cancer is selected from the group consisting of gastric cancer, lung cancer, colorectal cancer and melanoma.

Samples

The measurement of the level of phospho-Akt may be performed in vitro, on a sample of biological material derived from the subject. The sample may be any biological material separated from the body such as, for example, normal tissue, tumour tissue, cell lines, plasma, serum, whole blood, cerebrospinal fluid, lymph fluid, circulating tumour cells, cell lysate, tissue lysate, urine and aspirates. Preferably the sample is derived from the group consisting of normal tissue, tumour tissue, cell lines and circulating tumour cells. More preferably the sample is derived from tumour tissue or circulating tumour cells. In one particularly preferred embodiment the sample is derived from tumour tissue. For example, the level of phospho-Akt may be measured in a fresh, frozen or formalin fixed/paraffin embedded tumour tissue sample.

The sample is pre-obtained from the subject before the sample is subjected to the method steps involving measuring the level of the biomarker. The methods for removal of the sample are well known in the art, and it may for example be removed from the subject by biopsy, for example by punch biopsy, core biopsy, aspiration fine needle biopsy, endoscopic biopsy, or surface biopsy. A whole blood, plasma or serum sample may be collected by venipuncture and further processed according to standard techniques. Circulating tumour cells may also be obtained from blood based on, for example, size (e.g. ISET—Isolation by Size of Epithelial Tumour cells) or immunomagnetic cell enrichment (e.g. CellSearch®, Veridex, Raritan, N.J.).

Sample Comparison

The subject according to the invention may be human or animal. Preferably the subject is human.

The biomarker phospho-Akt is measured ex vivo in a sample or samples taken from the human or animal body, preferably taken from the human body. The sample or samples are pre-obtained from the human or animal body, preferably pre-obtained from the human body before the sample is subjected to the method steps involving measuring the level of the biomarker.

A biomarker is in general a substance that is used as an indicator of a biological response, preferably as an indicator of the susceptibility to a given treatment, which in the present application is treatment with a compound of general formula I or pharmaceutically acceptable derivatives thereof.

In a particularly preferred embodiment, higher phospho-Akt levels in the sample relative to a standard value or set of standard values predicts resistance.

The higher phospho-Akt levels may arise due to higher total Akt levels in the sample and/or a higher percentage of Akt which becomes phosphorylated.

As used herein, an increase or relatively high or high or higher levels relative to a standard level or set of standard levels means the amount or concentration of the biomarker in a sample is detectably greater in the sample relative to the standard level or set of standard levels. This encompasses at least an increase of, or higher level of, about 1% relative to the standard, preferably at least an increase of about 5% relative to the standard. More preferably it is an increase of, or higher level of, at least about 10% relative to the standard. More particularly preferably it is an increase of, or higher level of, at least about 20% relative to the standard. For example, such an increase of, or higher level of, may include, but is not limited to, at least about 1%, about 10%, about 20%, about 30%, about 50%, about 70%, about 80%, about 100%, about 150% or about 200% or more relative to the standard.

Preferably, higher phospho-Akt levels in a sample or samples
i) relative to a standard value or set of standard values from subjects with the same tumour histotype; or
ii) relative to a standard value or set of standard values from normal cells, tissue or body fluid;
are predictive of resistance.

The measuring of a level of phospho-Akt is performed ex-vivo in a sample pre-obtained from the subject.

Especially preferably, higher phospho-Akt levels in a sample or samples relative to a standard value or set of standard values from subjects with the same tumour histotype are predictive of resistance.

In one preferred embodiment, for the case i) where the measurement is compared in a sample or samples relative to a standard value or set of standard values from samples from subjects with the same tumour histotype as the sample to which it is to be compared, the standard value or set of standard values are established from samples from a population of subjects with that cancer type. The samples from these standard subjects may for example be derived from the tumour tissue or circulating tumour cells, as long as the origin of the sample is consistent between the standard and the sample to be compared.

In another preferred embodiment, for the case ii) where the measurement is compared in a sample or samples relative to a standard value or set of standard values taken from normal cells or tissue, the standard value or set of standard values may be established from a sample of normal (e.g. non-tumorous) cells, tissue or body fluid. Such data may be gathered from a population of subjects in order to develop the standard value or set of standard values.

The standard value or set of standard values are established ex-vivo from pre-obtained samples which may be from cell lines, or preferably biological material taken from at least one subject and more preferably from an average of subjects (e.g., n=2 to 1000 or more). The standard value or set of standard values may then be correlated with the response data of the same cell lines, or same subjects, to treatment with a compound of general formula I or a pharmaceutically acceptable derivative thereof. From this correlation a comparator module, for example in the form of a relative scale or scoring system, optionally including cut-off or threshold values, can be established which indicates the levels of biomarker associated with a spectrum of response levels to the compound of formula I or a pharmaceutically acceptable derivative thereof. The spectrum of response levels may comprise relative sensitivity to the therapeutic activity of the compound, (e.g. high sensitivity to low sensitivity), as well as resistance to the therapeutic activity. In a preferred embodiment this comparator module comprises a cut-off value or set of values which predicts resistance to treatment.

For example, if an immunohistochemical method is used to measure the level of phospho-Akt in a sample, standard values may be in the form of a scoring system. Such a system might take into account the percentage of cells in which staining for phospho-Akt is present. The system may also take into account the relative intensity of staining or cellular localisation in the individual cells. The standard values or set of standard values of the level of phospho-Akt may then be correlated with data indicating the response, especially resistance, of the subject or tissue or cell line to the therapeutic activity of a compound of formula I or a pharmaceutically acceptable derivative thereof. Such data may then form part of a comparator module.

Response is the reaction of the cell lines, or preferably of the subject, or more preferably of the disease in a subject, to the therapeutic activity of a compound of general formula I or a pharmaceutically acceptable derivative thereof. The spectrum of response levels may comprise relative sensitivity to the therapeutic activity of the compound, (e.g. high sensitivity to low sensitivity), as well as resistance to the therapeutic activity. The response data may for example be monitored in terms of: objective response rates, time to disease progression, progression free survival, and overall survival.

The response of a cancerous disease may be evaluated by using criteria well known to a person in the field of cancer treatment, for example but not restricted to:

Response Evaluation Criteria in Solid Tumors (RECIST) Guidelines, Source: Eisenhauer E A, Therasse P, Bogaerts J, Schwartz L H, Sargent D, Ford R, Dancey J, Arbuck S Gwyther S, Mooney M, Rubinstein L, Shankar L, Dodd L, Kaplan R, Lacombe D, Verweij J. New response evaluation criteria in solid tumours: revised RECIST guideline (version 1.1). Eur J. Cancer. 2009; 45:228-47;

RANO Criteria for High-Grade Gliomas, Source: Wen P Y, Macdonald D R, Reardon D A, Cloughesy T F, Sorensen A G, Galanis E, Degroot J, Wick W, Gilbert M R, Lassman A B, Tsien C, Mikkelsen T, Wong E T, Chamberlain M C, Stupp R, Lamborn K R, Vogelbaum M A, van den Bent M J, Chang S M. Updated response assessment criteria for high-grade gliomas: response assessment in neuro-oncology working group. J Clin Oncol. 2010; 28(11):1963-72;

CA-125 Rustin Criteria for Ovarian Cancer Response, Source: Rustin G J, Quinn M, Thigpen T, du Bois A, Pujade-Lauraine E, Jakobsen A, Eisenhauer E, Sagae S, Greven K, Vergote I, Cervantes A, Vermorken J. Re: New guidelines to evaluate the response to treatment in solid tumors (ovarian cancer). J Natl Cancer Inst. 2004; 96(6): 487-8;

and

PSA Working Group 2 Criteria for Prostate Cancer Response, Source: Scher H I, Halabi S, Tannock I, Morris M, Sternberg C N, Carducci M A, Eisenberger M A, Higano C, Bubley G J, Dreicer R, Petrylak D, Kantoff P, Basch E, Kelly W K, Figg W D, Small E J, Beer T M, Wilding G, Martin A, Hussain M; Prostate Cancer Clinical Trials Working Group. Design and end points of clinical trials for patients with progressive prostate cancer and castrate levels of testosterone: recommendations of the Prostate Cancer Clinical Trials Working Group. J Clin Oncol. 2008; 26(7):1148-59.

Resistance is associated with there not being an observable and/or measurable reduction in, or absence of, one or more of the following: reduction in the number of abnormal cells, preferably cancerous cells, or absence of the abnormal cells, preferably cancerous cells; for cancerous diseases: reduction in tumour size; inhibition (i.e., slowed to some extent and preferably stopped) of further tumour growth; reduction in the levels of tumour markers such as PSA and CA-125; inhibition (i.e., slowed to some extent and preferably stopped) of cancer cell infiltration into other organs (including the spread of cancer into soft tissue and bone); inhibition (i.e., slowed to some extent and preferably stopped) of tumour metastasis; alleviation of one or more of the symptoms associated with the specific cancer; and reduced morbidity and mortality.

In a preferred embodiment resistance means there is no observable and/or measurable reduction in, or absence of, one or more of the following criteria: reduction in tumour size; inhibition of further tumour growth; inhibition of cancer cell infiltration into other organs; and inhibition of tumour metastasis.

In a more preferred embodiment resistance refers to one or more of the following criteria: no reduction in tumour size; no inhibition of further tumour growth, no inhibition of cancer cell infiltration into other organs; and no inhibition of tumour metastasis.

Measurement of the aforementioned resistance criteria is according to clinical guidelines well known to a person in the field of cancer treatment, such as those listed above for measuring the response of a cancerous disease.

Response may also be established in vitro by assessing cell proliferation and/or cell death. For example, effects on cell death or proliferation may be assessed in vitro by one or more of the following well established assays: A) Nuclear staining with Hoechst 33342 dye providing information about nuclear morphology and DNA fragmentation which are hallmarks of apoptosis. B) Annexin V binding assay which reflects the phosphatidylserine content of the outer lipid bilayer of the plasma membrane. This event is considered an early hallmark of apoptosis. C) TUNEL assay (Terminal deoxynucleotidyl transferase mediated dUTP Nick End Labeling assay), a fluorescence method for evaluating cells undergoing apoptosis or necrosis by measuring DNA fragmentation by labeling the terminal end of nucleic acids. D) MTS proliferation assay measuring the metabolic activity of cells. Viable cells are metabolically active whereas cells with a compromised respiratory chain show a reduced activity in this test. E) Crystal violet staining assay, where effects on cell number are monitored through direct staining of cellular components. F) Proliferation assay monitoring DNA synthesis through incorporation of bromodeoxyuridine (BrdU). Inhibitory effects on growth/proliferation can be directly determined. G) YO-PRO assay which involves a membrane impermeable, fluorescent, monomeric cyanine, nucleic acid stain, which permits analysis of dying (e.g. apoptotic) cells without interfering with cell viability. Overall effects on cell number can also be analysed after cell permeabilisation. H) Propidium iodide staining for cell cycle distribution which shows alterations in distribution among the different phases of the cell cycle. Cell cycle arresting points can be determined. I) Anchorage-independent growth assays, such as colony outgrowth assays which assess the ability of single cell suspensions to grow into colonies in soft agar.

In a preferred embodiment relating to determination of resistance in vitro, resistance means there is no decrease in the proliferation rate of abnormal cells and/or reduction in the number of abnormal cells. More preferably resistance means there is no decrease in the proliferation rate of cancerous cells and/or no reduction in the number of cancerous cells. The reduction in the number of abnormal, preferably cancerous, cells may occur through a variety of programmed and non-programmed cell death mechanisms. Apoptosis, caspase-independent programmed cell death and autophagic cell death are examples of programmed cell death. However the cell death criteria involved in embodiments of the invention are not to be taken as limited to any one cell death mechanism.

phospho-Akt

As defined above, the term Akt is used herein to encompass all the previously mentioned synonyms and isoforms and phospho-Akt is Akt that has been phosphorylated on one or more residues, with the proviso that for Akt1, Akt2, and Akt3 the designation phospho-Akt is used to indicate phosphorylation at a site other than T308, T309 or T305 respectively. To clarify this further, the phospho-Akt may or may not be phosphorylated at T308, T309 or T305 for Akt 1, Akt 2 and Akt3 respectively, but the designation phospho-Akt indicates phosphorylation at sites other than these.

Preferred examples of the protein sequence of Akt (human Akt) are listed in SEQ. ID No. 1 to 3, FIGS. 9-11. However the term Akt also encompasses homologues, mutant forms, allelic variants, isoforms, splice variants and equivalents of these sequences. The human homologues, mutant forms, allelic variants, isoforms, splice variants and equivalents of these sequences are more preferred embodiments. More preferably it encompasses sequences having at least about 75% identity, especially preferably at least about 85% identity, particularly preferably at least about 95% identity, to any of the sequences represented by SEQ. ID. No. 1 to 3. In an especially preferred embodiment, Akt corresponds to any of the sequences represented by SEQ ID NO. 1 to 3 and sequences having at least 99% identity with any of these sequences. In a particularly preferred embodiment, Akt corresponds to the sequence represented by SEQ ID NO. 1 and sequences having at least 95% identity with this sequence, preferably at least 99% identity. In a more particularly preferred embodiment, Akt corresponds to a sequence represented by any of SEQ ID NO. 1 to 3. In a still more particularly preferred embodiment Akt corresponds to a sequence represented by SEQ ID NO. 1.

In a particularly preferred embodiment, phospho-Akt shall refer to Akt (wherein the preferred embodiments thereof are as given in the preceding paragraph) that has been phosphorylated on the following serine residue:

for Akt1 (SEQ. ID. No. 1): S473;
for Akt2 (SEQ. ID. No. 2): S474; and
for Akt3 (SEQ. ID. No. 3): S472.

In yet another especially preferred embodiment, phospho-Akt corresponds to any of the sequences represented by SEQ ID NO. 1 to 3 and sequences having at least 99% identity with any of these sequences, and wherein for the sequence represented by SEQ. ID. No. 1, S473 is phosphorylated, or for the sequence represented by SEQ. ID. No. 2, S474 is phosphorylated, or for the sequence represented by SEQ. ID. No. 3, S472 is phosphorylated.

In a very particularly preferred embodiment phospho-Akt corresponds to a sequence represented by SEQ ID NO. 1 that has been phosphorylated on S473.

Level of Phospho-Akt

The level of phospho-Akt may be assayed in the sample by technical means well known to a skilled person. Examples of methods of protein expression analysis known in the art which are suitable to measure the level of phospho-Akt at the protein level include, but are not limited to, i) immunohistochemistry (IHC) analysis, ii) western blotting iii) immunoprecipitation iv) enzyme linked immunosorbant assay (ELISA), v) radioimmunoassay, vi) Fluorescence activated cell sorting (FACS), vii) mass spectrometry, including matrix assisted laser desorption/ionization (MALDI, e.g. MALDI-MS) or electrospray (e.g. ESI-MS).

The antibodies involved in some of the above methods may be monoclonal or polyclonal antibodies, antibody fragments, and/or various types of synthetic antibodies, including chimeric antibodies. The antibody may be labeled to enable it to be detected or capable of detection following reaction with one or more further species, for example using a secondary antibody that is labeled or capable of producing a detectable result. Antibodies specific to phospho-Akt are available commercially from Cell Signaling or can be prepared via conventional antibody generation methods well known to a skilled person.

Preferred methods of protein analysis are ELISA, mass spectrometry techniques, immunohistochemistry and western blotting, more preferably ELISA, western blotting and immunohistochemistry, particularly preferably western blotting and immunohistochemistry. In western blotting, also known as immunoblotting, labelled antibodies may be used to assess levels of protein, where the intensity of the signal from the detectable label corresponds to the amount of protein, and can be quantified for example by densitometry.

Immunohistochemistry again uses labelled antibodies to detect the presence and relative amount of the biomarker. It can be used to assess the percentage of cells for which the biomarker is present. It can also be used to assess the localisation or relative amount of the biomarker in individual cells; the latter is seen as a function of the intensity of staining.

ELISA stands for enzyme linked immunosorbant assay, since it uses an enzyme linked to an antibody or antigen for the detection of a specific protein. ELISA is typically performed as follows (although other variations in methodology exist): a solid substrate such as a 96 well plate is coated with a primary antibody, which recognises the biomarker. The bound biomarker is then recognised by a secondary antibody specific for the biomarker. This may be directly joined to an enzyme or a third anti-immunoglobulin antibody may be used which is joined to an enzyme. A substrate is added and the enzyme catalyses a reaction, yielding a specific colour. By measuring the optical density of this colour, the presence and amount of the biomarker can be determined.

Uses of Biomarker

The biomarker may be used to predict inherent resistance of the disease in a subject to the compound of general formula I or a pharmaceutically acceptable derivative thereof as defined above.

The biomarker may be used to select subjects suffering or predisposed to suffering from a disease, preferably cancer, for treatment with a compound of general formula I or a pharmaceutically acceptable derivative thereof as defined above. The levels of such a biomarker may be used to identify subjects likely to respond or to not respond to treatment with such agents. Stratification of subjects may be made in order to avoid unnecessary treatment regimes. In particular the biomarker may be used to identify subjects from whom a sample or samples do not display a higher level of phospho-Akt, relative to a standard level or set of standard levels, whereupon such subjects may then be selected for treatment with the compound of formula I or a pharmaceutically acceptable derivative thereof as defined above.

The biomarker may also be used to assist in the determination of treatment regimes, regarding amounts and schedules of dosing. Additionally, the biomarker may be used to assist in the selection of a combination of drugs to be given to a subject, including a compound or compounds of general formula I or a pharmaceutically acceptable derivative thereof, and another chemotherapeutic (cytotoxic) agent or agents. Furthermore, the biomarker may be used to assist in the determination of therapy strategies in a subject including whether a compound of general formula I or a pharmaceutically acceptable derivative thereof is to be administered in combination with targeted therapy, endocrine therapy, radiotherapy, immunotherapy or surgical intervention, or a combination of these.

Phospho-Akt may also be used in combination with other biomarkers to predict the response to a compound of general formula I or a pharmaceutically acceptable derivative thereof and to determine treatment regimes. It may furthermore be used in combination with chemo-sensitivity testing to predict resistance and to determine treatment regimes. Chemo-sensitivity testing involves directly applying a compound of general formula I to cells taken from the subject, for example from a subject with haematological malignancies or accessible solid tumours, for example breast, head and neck cancers or melanomas, to determine the response of the cells to the compound.

Method of Treatment

The invention also involves in some aspects a method of treatment and phospho-Akt for use in a method of treatment, wherein the level of phospho-Akt is first established relative to a standard level or set of standard levels and then a compound of general formula I or a pharmaceutically acceptable derivative thereof as defined above, is administered if the level of phospho-Akt in said sample is not higher than a standard value or set of standard values. The compound of formula I or a pharmaceutically acceptable derivative thereof may be administered in a pharmaceutical composition, as is well known to a person skilled in the art. Suitable compositions and dosages are for example disclosed in WO 2004/103994 A1 pages 35-39, which are specifically incorporated by reference herein. Compositions for enteral administration, such as nasal, buccal, rectal or, especially, oral administration, and for parenteral administration, such as intravenous, intramuscular or subcutaneous administration, to warm-blooded animals, especially humans, are especially preferred. More particularly, compositions for intravenous administration are preferred.

The compositions comprise the active ingredient and a pharmaceutically acceptable carrier. An example of a composition includes, but is not limited to, the following: 5000 soft gelatin capsules, each comprising as active ingredient 0.05 g of one of the compounds of general formula (I), are prepared as follows: 250 g pulverized active ingredient is suspended in 2 liter Lauroglykol® (propylene glycol laurate, Gattefossé S.A., Saint Priest, France) and ground in a wet pulverizer to produce a particle size of about 1 to 3 μm. 0.419 g portions of the mixture are then introduced into soft gelatin capsules using a capsule-filling machine.

The invention also relates in one aspect to a method of treating a neoplastic or autoimmune disease, preferably cancer, by first decreasing the level of phospho-Akt in a subject that has a sample with a higher level of phospho-Akt compared to a standard level or set of standard levels, then treating the subject with a compound of general formula I or a pharmaceutically acceptable derivative as defined above. The level of phospho-Akt may be decreased by direct or indirect chemical or genetic means. Examples of such methods are treatment with a drug that results in reduced phospho-Akt levels, targeted delivery of viral, plasmid or peptide constructs or antibody or siRNA or antisense to downregulate the level of phospho-Akt. For example siRNA may be used to reduce the level of rictor expressed, thus reducing mTORC2 complex formation and activity, and thereby indirectly lower the level of phosphorylated Akt. The subject may then be treated with a compound of general formula I or a pharmaceutically acceptable derivative thereof.

A compound of general formula I or a pharmaceutically acceptable derivative thereof can be administered alone or in combination with one or more other therapeutic agents. Possible combination therapy may take the form of fixed combinations, or the administration of a compound of the invention and one or more other therapeutic agents which are staggered or given independently of one another, or the combined administration of fixed combinations and one or more other therapeutic agents. A compound of general formula I or a pharmaceutically acceptable derivative thereof can, besides or in addition, be administered especially for tumour therapy in combination with chemotherapy (cytotoxic), targeted therapy, endocrine therapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumour regression, or even chemo-preventive therapy, for example in patients at risk.

Kit and Device

In one aspect the invention relates to a kit, and in another aspect to a device, for predicting the response, preferably of a disease in a subject, to a compound of general formula I or a pharmaceutically acceptable derivative thereof as defined above, comprising reagents necessary for measuring the level of phospho-Akt in a sample. Preferably, the reagents comprise a capture reagent comprising a detector for phospho-Akt and a detector reagent.

The kit and device may also preferably comprise a comparator module which comprises a standard value or set of standard values to which the level of phospho-Akt in the sample is compared. In a preferred embodiment, the comparator module is included in instructions for use of the kit. In another preferred embodiment the comparator module is in the form of a display device, for example a strip of colour or numerically coded material which is designed to be placed next to the readout of the sample measurement to indicate resistance levels. The standard value or set of standard values may be determined as described above.

The reagents are preferably antibodies or antibody fragments which selectively bind to phospho-Akt. These may for example be in the form of one specific primary antibody which binds to phospho-Akt and a secondary antibody which binds to the primary antibody, and which is itself labelled for detection. The primary antibody may also be labelled for direct detection. The kits or devices may optionally also contain a wash solution(s) that selectively allows retention of the bound biomarker to the capture reagent as compared with other biomarkers after washing. Such kits can then be used in ELISA, western blotting, flow cytometry, immunohistochemical or other immunochemical methods to detect the level of the biomarker.

Furthermore the device may comprise imaging devices or measurement devices (for example, but not restricted to, measurement of fluorescence) which further process the measured signals and transfer them into a scale in a comparator module.

More preferably the kit comprises a compound of general formula I, or a pharmaceutically acceptable derivative thereof as defined above. This compound may then be administered to the subject, in accordance with the level of the biomarker in the sample from the subject, as measured by the reagents comprised in the kit. Therefore the kit according to the invention may be used in the method of treatment according to the invention, as defined above. In an especially preferred embodiment the kit comprises a compound of the following formula or a pharmaceutically acceptable salt thereof

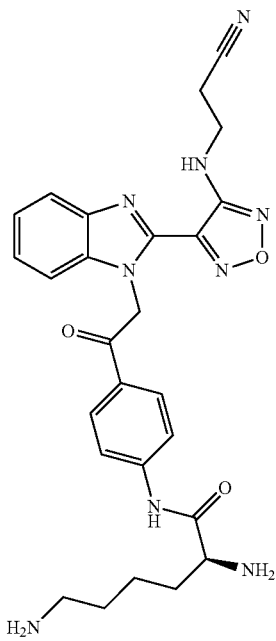 [SMILES: N#CCCNc1nonc1-c1nc2ccccc2n1CC(=O)c1ccc(NC(=O)[C@@H](N)CCCCN)cc1]

In a particularly preferred embodiment of the kit the pharmaceutically acceptable salt is a dihydrochloride salt. In another aspect the invention relates to the use of such a kit as described above.

In the present specification the words "comprise" or "comprises" or "comprising" are to be understood as to imply the inclusion of a stated item or group of items, but not the exclusion of any other item or group of items.

Experimental Methodology

Immunofluorescent Staining of Cultured Cells

A549 human non-small cell lung cancer (NSCLC, ATCC reference number CCL-185) cells, HeLa cervical cancer cells (ATCC reference number CCL-2) and SKBR3 breast carcinoma cells (ATCC reference number HTB-30) were seeded at densities of 50% on round microscope coverslips and cultured for 24 hours in RPMI-1640 containing 10% FCS (also referred to as FBS) at 37° C., 5% $CO_2$. Compounds to be tested were dissolved in DMSO. The cell culture medium was replaced with medium containing the diluted compound(s) (paclitaxel, vinblastine, colchicine and nocodazole were purchased from Sigma-Aldrich) or vehicle. After treatment for the times indicated in the Brief Description of the Figures, coverslips were washed and cells were fixed in methanol/acetone (1:1) for 5 minutes at room temperature and subsequently incubated in blocking buffer (0.5% BSA and 0.1% TX-100 in PBS) for 30 minutes at room temperature. Specimens were then incubated with anti-alpha-tubulin antibody (Sigma, 1:2000) for 1 hour at room temperature in blocking buffer. After several washing steps cells were incubated with AlexaFluor-488 goat-anti-mouse IgG (Molecular Probes, 1:3000) for 1 hour at room temperature followed by several washing steps with blocking buffer. Specimens were then mounted with ProLong Gold antifade (Molecular Probes), sealed with nail polish and examined with a Leica immunofluorescence microscope. Images were captured with a cooled CCD-camera and processed by ImageJ software.

Colony Outgrowth Assay:

Single cell suspensions of patient-derived tumour xenografts (maintained in nude mice) were prepared. For colony outgrowth assays, cells were plated in soft agar in 24-well plates according to the assay introduced by Hamburger & Salmon (Primary bioassay of human tumour stem cells, Science, 1977, 197:461-463). $2 \times 10^4$-$6 \times 10^4$ cells in 0.2 mL medium containing 0.4% agar were plated out on a bottom layer of 0.75% agar. Test compounds were applied in 0.2 mL culture medium. Every 24-well plate contained untreated controls and samples in triplicates. Cultures were incubated at 37° C. and 7.5% $CO_2$ for 5-28 days. 24 hours prior to analysis, vital colonies were stained with a solution of metabolizable tetrazolium salt (Alley M C et al, Life Sci. 1982, 31:3071-3078) and were counted with an automatic image analysis system (Omnicon 3600, Biosys GmbH).

Relative drug effects were expressed by the ratio of the mean number of colonies in the treated wells and the control wells. $IC_{70}$-values were determined by plotting compound concentrations versus relative colony counts.

Protein Extraction

Tumours were extracted in ice-cold buffer containing 50 mM HEPES (pH 7.5), 150 mM NaCl, 25 mM β-glycerophosphate, 25 mM NaF, 5 mM EGTA, 1 mM EDTA, 0.1% NP40, 15 mM pyrophosphate, 2 mM sodium orthovanadate, 10 mM sodium molybdate, leupeptin (10 μg/mL), aprotinin (10 μg/mL) and 1 mM PMSF (1 mL extraction volume per 45 mg tumour). After homogenisation by Polytron, lysates were adjusted to 1% NP40 and incubated on ice for 20 min. Lysates were clarified by centrifugation and frozen at −80° C.

Immunoblotting/Western Blotting

Immunoblotting was performed using 20 μg of total protein per lane. Protein concentration was determined with the BCA Protein Assay (Pierce). Protein was separated on a 10% SDS-gel and transferred to a PVDF membrane using Wet Blotting (45 min, 250 mA/gel). The primary antibodies used for immunoblotting were as follows:

Phospho-Akt (serine 473) (available from Cell Signalling, reference number 9271) origin: rabbit polyclonal antibody, dilution 1:1000, buffer conditions: PBS containing 0.5% milk/0.1% tween;

Akt protein (available from Epitomics, reference number 1085-1) origin: rabbit monoclonal antibody, dilution 1:2000, buffer conditions: PBS containing 0.5% milk/0.1% tween;

Actin: (available from Chemicon, reference number MAB1501) origin: mouse, monoclonal, dilution 1:5000, buffer conditions: PBS containing 0.5% milk/0.1% tween.

The secondary antibodies used for immunoblotting were peroxidase-conjugated goat anti-rabbit or goat anti-mouse (available from Jackson ImmunoResearch Laboratories INC: reference number 111-035-144 JIR and 115-035-146 JIR), dilution 1:5000, buffer conditions: 0.5% milk in PBS/0.1° A Tween. Labelled bands were revealed using a Raytest Stella 3200 High Performance Imaging System.

Immunohistochemistry

Fixation of patient-derived tumour xenografts (maintained in nude mice) was performed in 10% neutral-buffered formalin containing 4% formaldehyde for 20-28 hours at room temperature. Fixed specimens were kept in a solution of 70% ethanol for a maximum of one week prior to dehydration and paraffin embedding according to a standard procedure, using the conditions listed below:

| Sequential Treatment | time (hours) |
| --- | --- |
| 70% EtOH | 1 |
| 80% EtOH | 2 |
| 99% EtOH | 1 |
| 100% Isopropanol | 0.5 |
| 100% Isopropanol | 1 |
| Xylol | 0.5 |
| Xylol | 1 |
| Xylol | 1 |
| Paraffin | 1 |
| Paraffin | 2 |
| Paraffin | 2 |

Paraffin sections of approximately 2 μm were cut and processed by using the automated immunostainer Benchmark XT® (Roche) running the standard processing steps. The visualisation of the specific antibody staining was done with DAB (3,3-diaminobenzidine) as chromogenic substrate at a concentration of 5 mg/mL. The following primary antibody and processing conditions were used for staining:

| Antibody Specification | Processing |
| --- | --- |
| Anti-Akt-pS473 from Dako, # M3628 rabbit monoclonal antibody | MTec100/30: EDTA-citrate buffer retrieval pH 8, 100° C. for 30 minutes. Antibody incubation at 37° C. for 32 minutes at a dilution of 1:20 |

DETAILED EXAMPLES

Example 1

A Distinct Mitotic Phenotype Induced by Compounds of General Formula I

Figure 2:
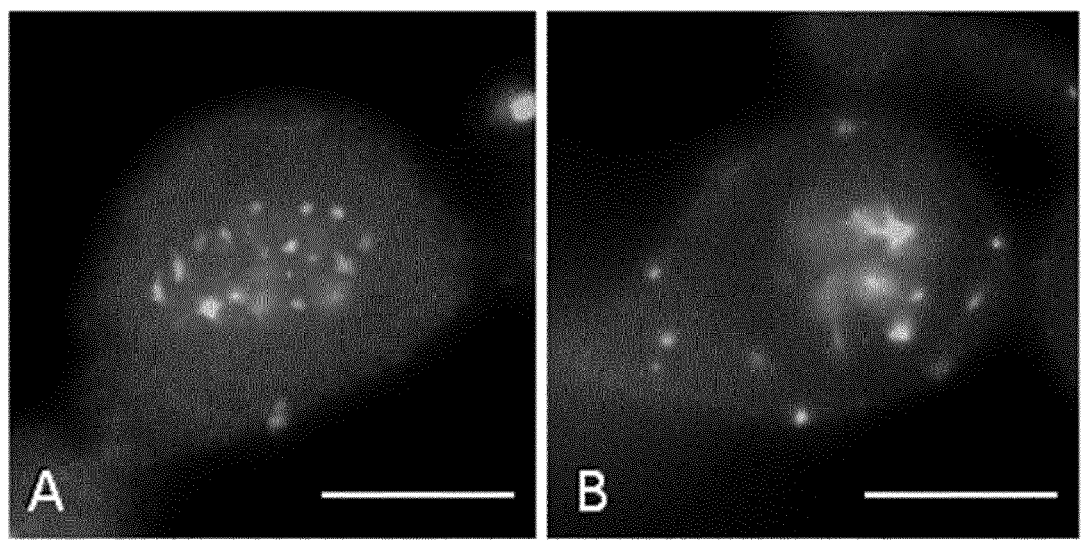
FIG. 2: Shows the treatment of A549 NSCLC cells with the Compounds B and C. The microtubules of mitotic or G2/M arrested A549 NSCLC cells were stained after 24 hours treatment with 80 nM or 20 nM of Compounds B and C, respectively. The white scale bar represents 10 micrometers.
Figure 3:
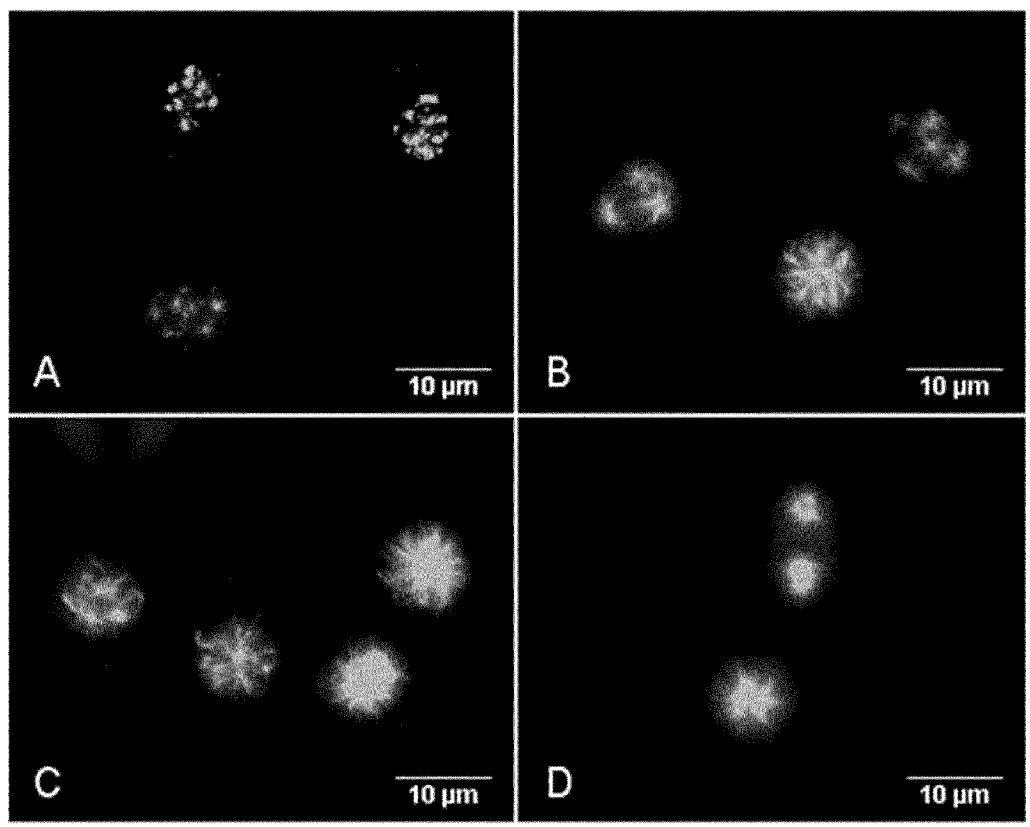
FIG. 3: Shows a comparison of treatment of cells with BAL27862 compared to conventional microtubule targeting agents. Microtubules of mitotic or G2/M arrested A549 NSCLC cells were stained after 24 hours of treatment with 50 nM of A: BAL27862; B: vinblastine; C: colchicine; D: paclitaxel. Stacks of images taken every 1 μm were processed by using ImageJ software.
Figure 4:
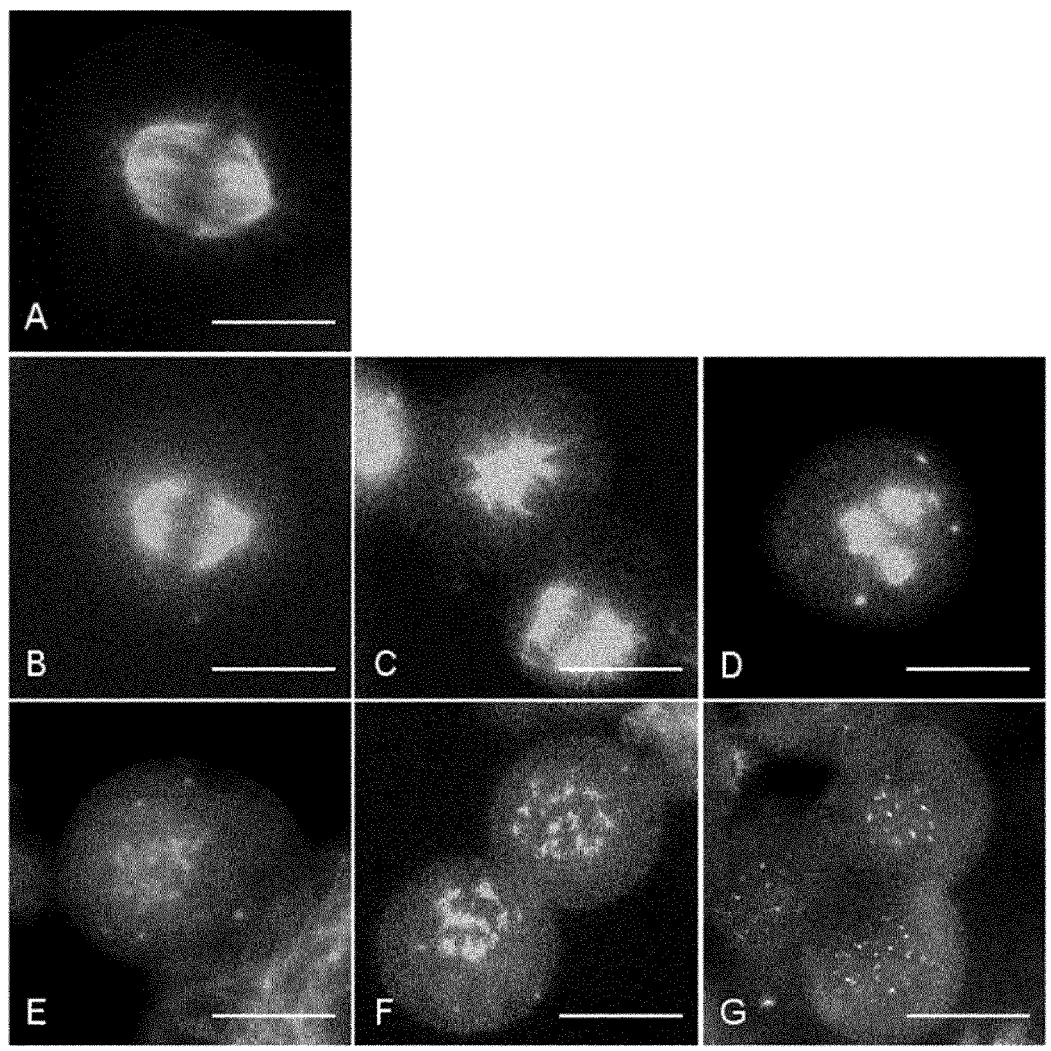
FIG. 4: Shows a comparison of treatment of A549 NSCLC cells with BAL27862 compared to nocodazole. Microtubules of mitotic or G2/M arrested cells were stained after 24 h of treatment with various concentrations of nocodazole (B, C & D) and BAL27862 (E, F & G). A: control, B: Nocodazole 50 nM, C: Nocodazole 100 nM, D: Nocodazole 200 nM, E: BAL27862 20 nM; F: BAL27862 30 nM and G: BAL27862 50 nM. The white scale bar represents 10 micrometers. Representative images of the microtubule phenotypes observed are shown.

Treatment with compound A (BAL27862) or with compound B, or compound C induced a highly reproducible and distinct microtubule phenotype in all tumour cell lines tested (shown for BAL27862 in A549, HeLa and SKBR3 cells in FIG. 1, and for compound C and compound B in A549 cells in FIG. 2). In dividing cells an apparent fragmentation of the mitotic spindle occurred, resulting in the formation of dot-like structures (FIG. 1). This phenotype was shown to be distinct from that observed with conventional microtubule targeting agents, such as the microtubule stabiliser paclitaxel and the microtubule destabilisers vinblastine and colchicine (FIG. 3) and nocodazole (FIG. 4).

Example 2

Figure 5:
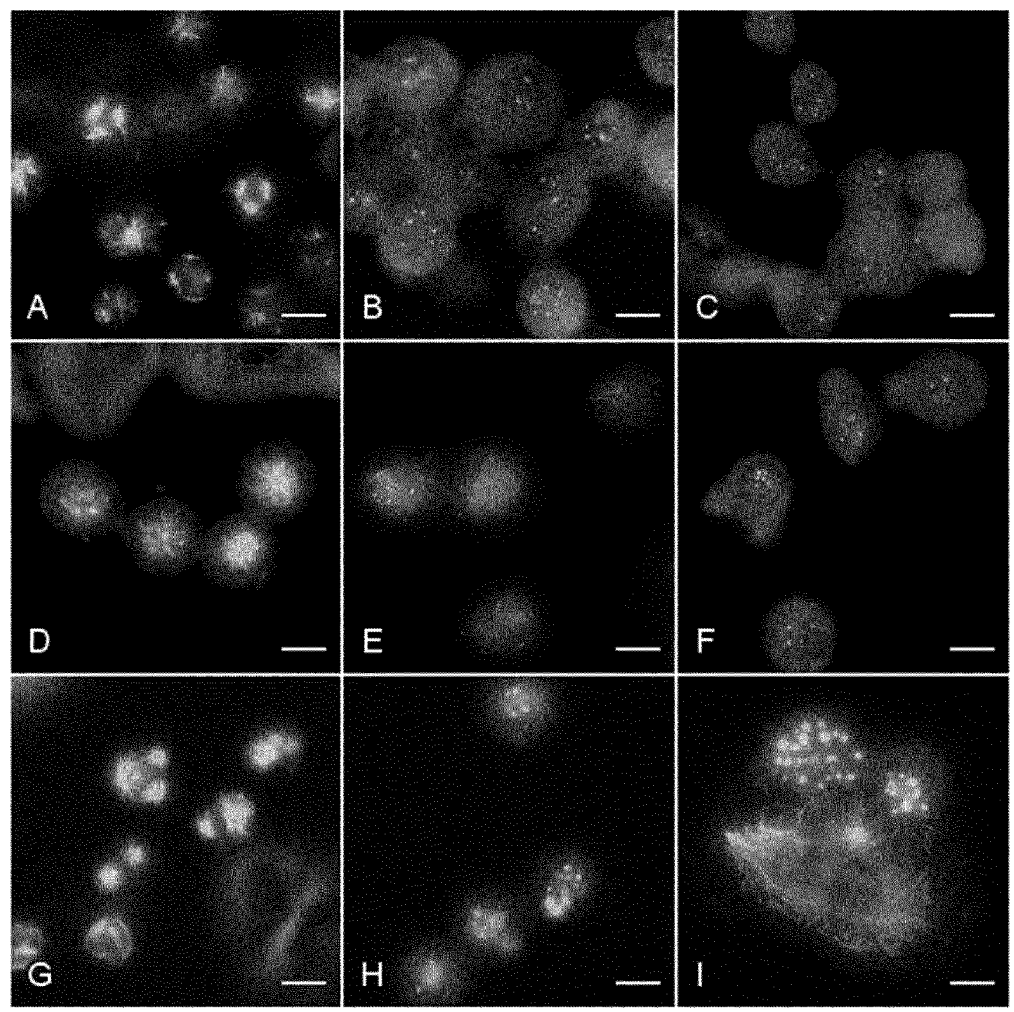
FIG. 5: Shows a combination of treatment with BAL27862 and conventional microtubule-targeting agents. Microtubules of mitotic or G2/M arrested A549 NSCLC cells were stained after treatment for the times indicated below. 50 nM BAL27862, 50 nM vinblastine, 50 nM colchicine and 25 nM paclitaxel were used. The white scale bar represents 10 micrometers.
Figure 6:
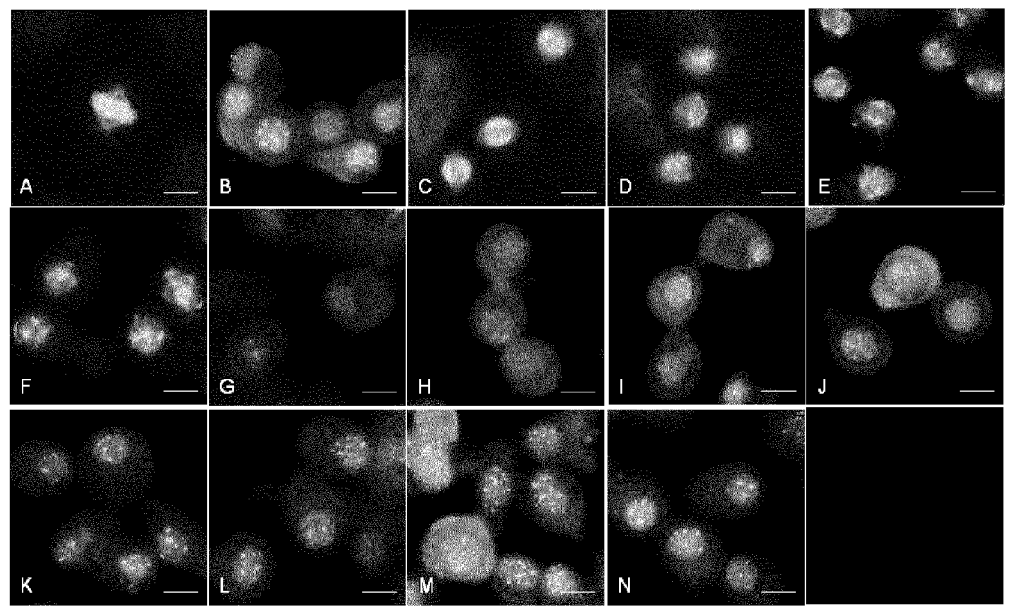
FIG. 6: Shows a combination of treatment with BAL27862 and nocodazole. Microtubules of mitotic or G2/M arrested A549 NSCLC cells were stained after treatment for the times indicated below. 25 nM BAL27862 and nocodazole at the concentrations indicated below were used. The white scale bar represents 10 micrometers.

BAL27862 Overcomes Microtubule Phenotype Induced by Conventional Microtubule-targeting Drugs in a Dominant Fashion In order to show the uniqueness of its activity on microtubules, BAL27862 was tested in combination with vinblastine, colchicine and paclitaxel (FIG. 5) and nocodazole (FIG. 6) using A549 cells. Treatment with vinblastine, colchicine, paclitaxel or nocodazole alone induced the mitotic microtubule phenotypes characteristic of these agents. However, combination treatment with BAL27862 for the last 4 hours resulted in disruption of the microtubule structures; creating a phenotype consistent with treatment of BAL27862 alone, despite the continued presence of vinblastine, colchicine, paclitaxel or nocodazole. In contrast, treating first with BAL27862 and subsequently for 4 hours in combination with vinblastine, colchicine, paclitaxel or nocodazole had no impact on the observed microtubule phenotype that was consistent with treatment with BAL27862.

These data demonstrate that compounds of formula I affect microtubule biology consistently, but in a different manner than conventional microtubule targeting agents.

Detailed Examples According to the Invention

Example 3

Association of High Phospho-Akt Expression Levels with Patient-Derived Tumour Cells Resistant to BAL27862 Treatment Based on colony outgrowth assays, using tumour cells derived from 8 patient-derived tumours maintained as xenografts in mice, BAL27862-sensitive or resistant tumour cells were identified from gastric cancer, colorectal cancer, melanoma, and lung cancer (see Table 1). Concentrations at which 70% growth inhibition was observed versus controls ($IC_{70}$) are shown in Table 1. In this table, BAL27862-sensitive tumour cells were those that had $IC_{70}$ values in the low nanomolar range, while BAL27862-resistant tumour cells had $IC_{70}$ values >600 nanomolar. Paclitaxel and vinblastine data, using the same ex vivo assay, was available for 7 of the 8 tumour models. Of these 7 models, all were resistant to treatment with paclitaxel, while 6 were sensitive to treatment with vinblastine.

for GXF 97 the levels were clearly higher. The same lack of association was true for the vinca alkaloid, vinblastine, in the gastric models, since both these tumours were sensitive to vinblastine. This lack of association was repeated in the melanoma and colorectal cancer models. Thus phospho-Akt levels were shown to be unsuitable as a reliable biomarker of resistance to the conventional microtubule agents paclitaxel and vinblastine in patient-derived tumour models.

Figure 7:
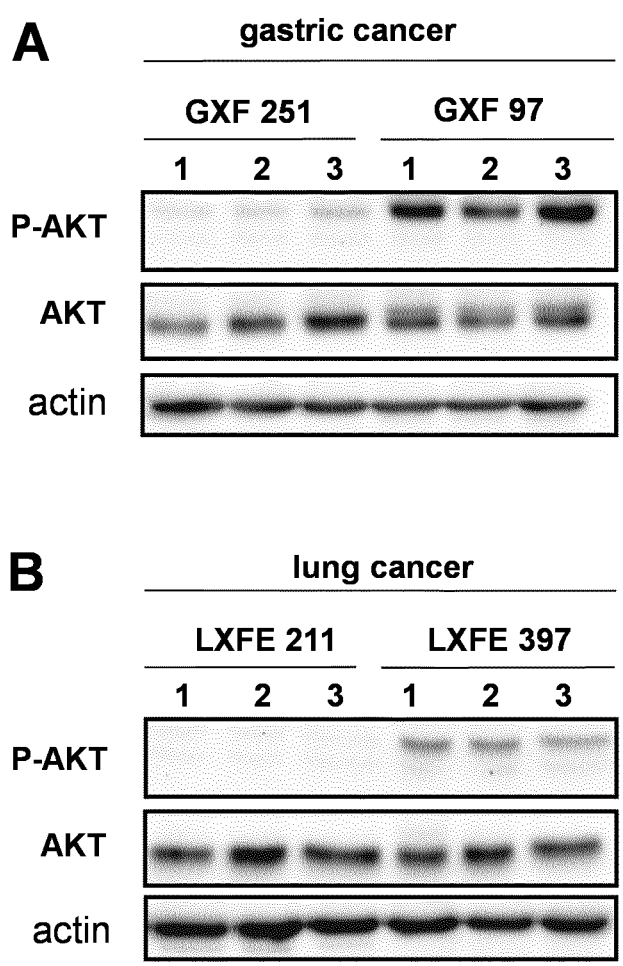
FIG. 7: Shows protein extracts prepared from patient-derived gastric cancer (FIG. 7A), lung cancer (FIG. 7B), colorectal cancer (FIG. 7C) and melanoma (FIG. 7D) tumours obtained from subcutaneously xenografted nude mice, and analysed by immunoblotting for phospho-Akt and Akt expression, with actin included as a loading control. Three independent tumours were analysed in each case (1-3). BAL27862, paclitaxel and vinblastine resistance and sensitivity of the tumour cells using an ex vivo colony outgrowth assay is as defined in Table 1.
Figure 7:
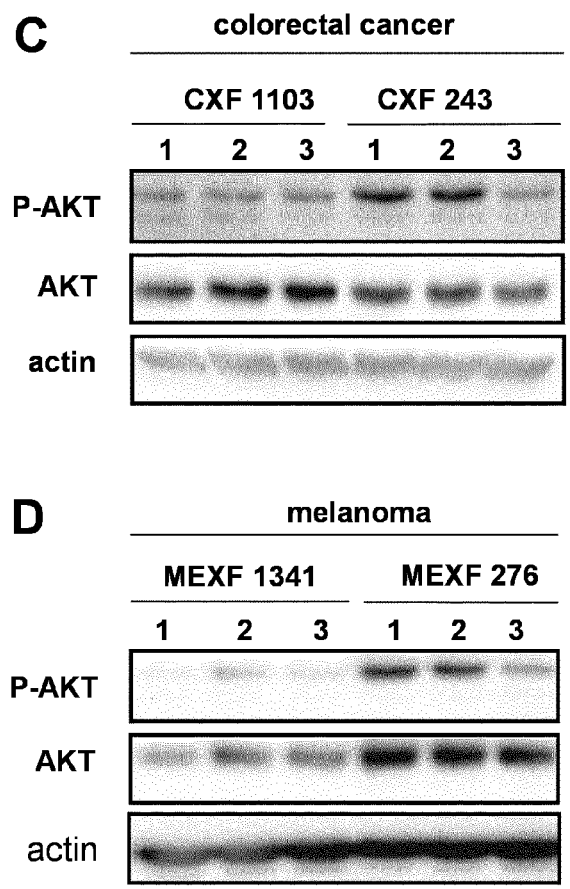

Surprisingly, in contrast, when the BAL27862 resistance data, as defined by the colony outgrowth assay, was compared with the phospho-Akt level, phospho-Akt expression was shown to be higher only in the resistant tumours and not in the sensitive tumours derived from the same tumour histotype (compare FIG. 7 with Table 1). Increased expression levels were therefore consistently indicative of resistance to BAL27862. Thus phospho-Akt levels were shown to be a biomarker of resistance for the compound according to the invention, BAL27862.

Example 4

Immunohistochemical Analysis of Gastric Tumour Xenografts

Figure 8:
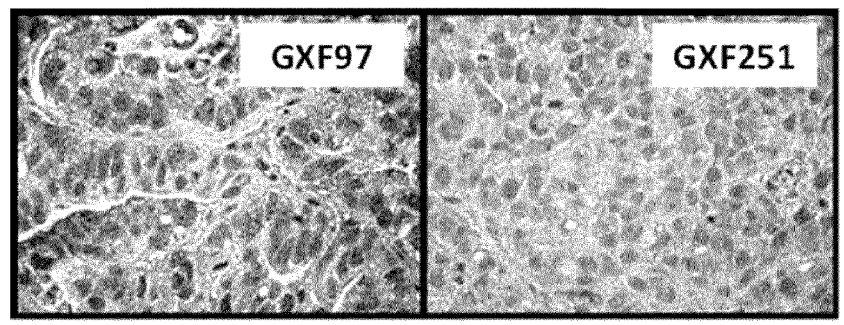
FIG. 8: Shows that tumour cell phospho-Akt levels are increased in a patient-derived xenografted gastric tumour model defined as BAL27862 resistant by ex vivo colony outgrowth analysis. Patient-derived tumour xenografts (maintained in nude mice) were prepared, fixed and stained for phospho-Akt protein expression using immunohistochemistry. BAL27862, paclitaxel and vinblastine resistance and sensitivity of the tumour cells using an ex vivo colony outgrowth assay is as defined in Table 1.

Immunohistocehmical analysis was performed on the gastric tumour xenografts (FIG. 8), revealing a higher level of phospho-Akt in the tumour model GXF 97. Again a clear correlation was seen between higher levels of phospho-Akt and resistance to BAL27862 (tumour model GXF 97 was BAL27862-resistant, while tumour model GXF 251 was BAL27862-sensitive; as defined by the colony outgrowth assay—Table 1). Thus phospho-Akt levels were again shown to be a biomarker of resistance for the compound according to the invention, BAL27862.

LIST OF ABBREVIATIONS

A549 human non-small cell lung cancer cell line
BCA bicinchoninic acid

TABLE 1

| Cancer type | name | Response to BAL27862 | $IC_{70}$ BAL27862 [micromolar] | Response to paclitaxel | Response to vinblastine |
|---|---|---|---|---|---|
| Gastric | GFX 251 | sensitive | 0.485 | resistant | sensitive |
| Gastric | GFX 97 | resistant | >3.5 | resistant | sensitive |
| Lung | LXFE 211 | sensitive | 0.021 | resistant | sensitive |
| Lung | LXFE 397 | resistant | >3.5 | Not known | Not known |
| Melanoma | MEXF 1341 | sensitive | 0.025 | resistant | sensitive |
| Melanoma | MEXF 276 | resistant | >3.5 | resistant | sensitive |
| Colorectal cancer | CXF 1103 | sensitive | 0.022 | resistant | resistant |
| Colorectal cancer | CXF 243 | resistant | 0.696 | resistant | sensitive |

Immunoblotting analysis was performed in order to measure the levels of phospho-Akt (using an antibody recognising phosphorylated serine-473) and Akt protein in the same tumours maintained as xenografts. The actin levels were included on the immunoblot as a loading control.

Analysis of phospho-Akt levels indicated that phospho-Akt levels varied across the tumours (FIG. 7).

Based on the colony outgrowth assay and the same $IC_{70}$ criteria, there was no association between paclitaxel or vinblastine resistance and high phospho-Akt expression levels (compare FIG. 7 with Table 1). This is evident, for example, in the gastric cancer models. Although GXF 251 and GXF 97 were both resistant to paclitaxel, for GXF 251 the phospho-Akt levels were virtually undetectable, while BrdU bromodeoxyuridine
BSA bovine serum albumin
CA-125 cancer antigen 125
CCD charge-coupled device
CREST limited scleroderma syndrome
DAB 3,3-diaminobenzidine
DMSO dimethylsulphoxide
DNA deoxyribonucleic acid
dUTP 2'-Deoxyuridine 5'-Triphosphate
EDTA ethylenediaminetetraacetic acid
EGTA ethyleneglycol-bis(β-aminoethyl)-N,N,N',N'-tetraacetic acid
ELISA enzyme-linked immunosorbent assay
ESI-MS electrospray ionization mass spectrometry EtOH ethanol
FACS fluorescence activated cell scan/sorting
FCS/FBS foetal calf/foetal bovine serum
G2/M transition from G2 to the mitotic phase in the cell cycle
HeLa human squamous cell cancer cell line
HEPES 4-(2-Hydroxyethyl)piperazine-1-ethanesulphonic acid
Hoe33342 2'-(4'-Ethoxyphenyl)-5-(4-methylpiperazin-1-yl)-2,5'-bis-1H-benzimidazole trihydrochloride trihydrate
$IC_{70}$ concentration at which 70% signal is inhibited
IgG immunoglobulin G
IHC immunohistochemistry
ISET isolation by size of epithelial tumor cells
MALDI matrix-assisted-laser-desorption/ionisation mass-spectrometry
mTORC2 mammalian target of rapamycin complex2
MTS 3-(4,5-dimethylthiazol-2-yl)-5-(3-carboxymethoxyphenyl)-2-(4-sulphophenyl)-2H-tetrazolium
NaF sodium fluoride
NCBI National Center for Biotechnology Information
NSCLC non-small cell lung cancer
NP40 Nonidet P40
PBS phosphate buffered saline
P-gp P-glycoprotein
PKB protein kinase B
PMSF phenylmethylsulphonyl fluoride
PSA prostate-specific antigen
PVDF polyvinylidene fluoride
RAC related to A and C kinases
RANO response assessment for high-grade gliomas
RECIST response evaluation criteria in solid tumors
RICTOR Rapamycin-insensitive companion of mTOR
RPMI-1640 cell culture medium used for culturing transformed and non-transformed eukaryotic cells and cell lines
SDS sodium dodecyl sulphate
SEQ. ID No. sequence identification number
siRNA small inhibitory ribonucleic acid
SKBR3 human mammary carcinoma cell line
TUNEL terminal deoxynucleotidyl transferase dUTP nick end labeling
Tween non-ionic detergent
YO-PRO fluorescent, monomeric cyanine, nucleic acid stain

The invention claimed is:

1. A method of determining whether a subject is resistant to treating a disease by administration to said subject a compound of formula I

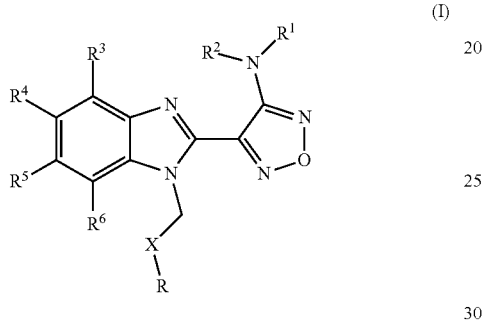

wherein

R represents phenyl, thienyl or pyridinyl wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxy-carbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;

and wherein pyridinyl is optionally substituted by lower alkoxy, amino or halogen;

X-represents a group C=Y, wherein Y is oxygen or nitrogen substituted by hydroxy or lower alkoxy;

or when R is optionally substituted phenyl or optionally substituted pyridinyl, X is alternatively oxygen;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

wherein the term "lower" denotes a radical having up to 7 carbon atoms;

or pharmaceutically acceptable salts, esters and amides of naturally occurring amino acids, small peptides or pegylated hydroxy acids; salts of such esters and amides; and isomers of the compound of formula I; said method comprising:

a) obtaining a sample from said subject;

b) measuring the level of the phospho-Akt proteins in said sample, said phospho-Akt proteins being selected from the group consisting of phospho-Akt1phospho-Akt2; and phospho-Akt3, wherein the phospho-Akt proteins contain at least one phosphorylation at a site other than T308 of phospho-Akt1, T309 of phospho-Akt2 and T305 of phospho-Akt3 respectively; and c) thereby determining from said measured level of the phospho-Akt proteins whether the subject is resistant to treating of said disease with said compound of formula I, or pharmaceutically acceptable salts, esters and amides of naturally occurring amino acids, small peptides or pegylated hydroxy acids; salts of such esters and amides; and isomers of the compound of formula I;

wherein said disease is a neoplastic disease selected from the group consisting of epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-,lobular and medullary neoplasms, acinar cell neoplasms, complex epithelial neoplasms, specialized gonadal neoplasms, paragangliomas and glomus tumours, naevi and melanomas, soft tissue tumours and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumours, lymphatic vessel tumours, osseous and chondromatous neoplasms, giant cell tumours, miscellaneous bone tumours, odontogenic tumours, gliomas, neuroepitheliomatous neoplasms, meningiomas, nerve sheath tumours, granular cell tumours and alveolar soft part sarcomas, Hodgkin's and non-Hodgkin's lymphomas, other lymphoreticular neoplasms, plasma cell tumours, mast cell tumours, immunoproliferative diseases, leukemias, miscellaneous myeloproliferative disorders, lymphoproliferative disorders and myelodysplastic syndromes.

2. The method of claim 1 wherein the phospho-Akt proteins are also phosphor fated at site T308 of phospho-Akt1, T309 of phospho-Akt2 and T305of phospho-Akt3 respectively.

3. The method of claim 1, wherein said subject is a human or animal, said sample is taken from the human or animal body, and the level of phospho-Akt proteins in said sample is measured ex vivo.

4. The method of claim 3, wherein the sample is derived from tumour tissue, normal tissue, circulating tumour cells, cell lines, plasma, whole blood or serum.

5. The method of claim 4, wherein the subjects is a human.

6. The method of claim 5, wherein the protein sequence of said phospho-Akt proteins is selected from the group consisting of SEQ ID No. 1, SEQ ID 2, SEQ ID 3 and homologues, mutant forms, allelic variants, isoforms, splice variants and proteins with sequences having at least 75% identity to SEQ ID 1, SEQ ID 2, or SEQ ID 3.

7. The method of claim 6, wherein said phospho-Akt proteins are also phosphorylated at site T308 of SEQ ID1, T309 of SEQ ID2 and T305 of SEQ ID3 respectively.

8. The method of claim 6, wherein said phospho-Akt proteins are phosphorylated on the following serine residue: for SEQ ID1: S473; for SEQ ID2: S474; and for SEQ-ID3: S472.

9. The method of claim 8, wherein said phospho-Akt proteins are also phosphorylated on the following threonine residue: for SEQ ID1: T308; for SEQ ID2: T309; and for SEQ ID3: T305.

10. The method of claim 3, wherein the determination of a higher level of phospho-Akt proteins in the sample from a subject relative to a standard value or values of phospho-Akt protein levels predicts resistance to treating said disease with said compound of formula I or pharmaceutically acceptable salts; esters and amides of naturally occurring amino acids, small peptides or pegylated hydroxy acid; salts of such esters and amides; and isomers of the compound of formula I.

11. The method of claim 8, wherein the protein sequence of the phospho-Akt is selected from the group consisting of SEQ ID No. 1, SEQ ID 2, SEQ ID 3, and homologues, mutant forms, allelic variants, isoforms, splice variants and proteins with sequences having at least 75% identity to SEQ ID 1, SEQ ID 2 or SEQ ID 3.

12. The method of claim 10, wherein the measured phospho-Akt protein levels in said sample is determined by comparing the measured phospho-Akt protein levels in said sample with:
   i) a standard value or a set of standard values of phospho-Akt protein levels from samples of subjects with the same tumour histotype; or
   ii) a standard value or a set of standard values of phospho-Akt protein levels from normal cells, tissues or body fluids.

13. The method of claim 1 wherein the neoplastic disease is selected from the group consisting of breast cancer, prostate cancer, cervical cancer, ovarian cancer, gastric cancer, colorectal cancer, pancreatic cancer, liver cancer, brain cancer, neuroendocrine cancer, lung cancer, kidney cancer, hematological malignancies, melanoma and sarcomas.

14. The method of claim 10, wherein the measured phospho-Akt protein levels in said sample is determined by comparing the measured phospho-Akt protein levels in said sample with:
   a standard value or a set of standard values of phospho-Akt protein levels from samples of subjects with the same tumor histotype; or
   a standard value or a set of standard values of phospho-Akt protein levels from normal tissues or cells.

15. The method of claim 1, wherein the compound is a compound of general formula I wherein
   R represents phenyl or pyridinyl
   wherein phenyl is optionally substituted by one or two substituents independently selected from lower alkyl, lower alkoxy, amino, acetylamino, halogen and nitro; and wherein pyridinyl is optionally substituted by amino or halogen;
   X represents a group C=O;
   $R^1$ represents hydrogen or cyano-lower alkyl;
   $R^2$, $R^3$, $R^4$, $R^5$ and R represent hydrogen;
   or pharmaceutically acceptable salts, esters and amides of naturally occurring amino acids, small peptides or pegylated hydroxy acids; salts of such esters and amides; and isomers of the compound of formula I.

16. The method of claim 1, wherein the compound is represented by the following formula

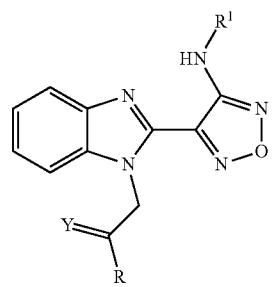

wherein R, Y and $R^1$ are defined as follows:

| R | Y | $R^1$ |
|---|---|---|
| H₂N–⟨phenyl⟩– | O | CH₂CH₂CN |
| H₂N–⟨phenyl⟩– | O | H |
| H₂N–⟨pyridinyl⟩– | O | CH₂CH₂CN | or pharmaceutically acceptable salts, esters and amides of naturally occurring amino acids, small peptides or pegylated hydroxy acids; salts of such esters and amides; and isomers of the compound of formula I.

17. The method of claim 1, wherein the compound is

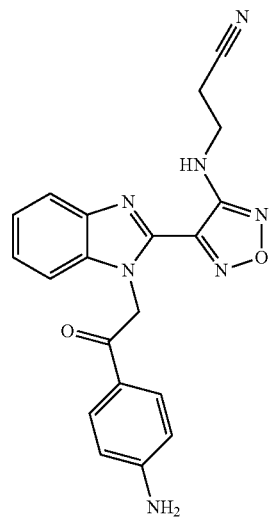 [SMILES: N#CCCNc1nonc1-c1nc2ccccc2n1CC(=O)c1ccc(N)cc1]

or pharmaceutically acceptable derivatives thereof salts, esters and amides of naturally occurring amino acids, small peptides or pegylated hydroxy acids; salts of such esters and amides; and isomers of the compound of formula I.

18. The method of claim 1, wherein the compound is

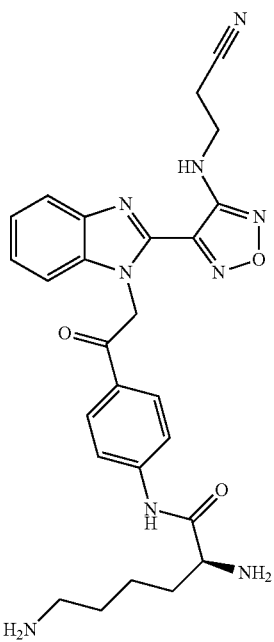 [SMILES: N#CCCNc1nonc1-c1nc2ccccc2n1CC(=O)c1ccc(NC(=O)[C@@H](N)CCCCN)cc1]

or a pharmaceutically acceptable salt thereof.

19. A method for predicting the response to treatment of a disease in a patient by administration of a compound of general formula I

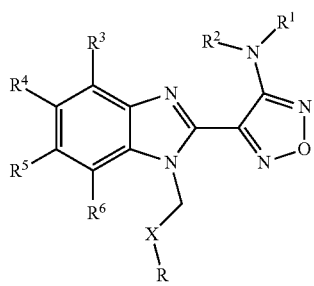

wherein

R represents phenyl, thienyl or pyridinyl
wherein phenyl is optionally substituted by one or two substituents independently selected from the group consisting of alkyl, halo-lower alkyl, hydroxy-lower alkyl, lower alkoxy-lower acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;

and wherein pyridinyl is optionally substituted by lower alkoxy, amino or halogen;

X represents a group C=Y,
wherein Y is oxygen or nitrogen substituted by hydroxy or lower alkoxy; or when R is optionally substituted phenyl or optionally substituted pyridinyl, X is alternatively oxygen, $R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower aikoxy;

or $R^4$ and $R^5$ together represent methylenedioxy;

or pharmaceutically acceptable salts, esters and amides of naturally occurring amino acids, small peptides or pegylated hydroxy acids, salts of such esters and amides; and isomers of the compound of general formula I, and wherein the term "lower" denotes a radical having up to 7 carbon atoms, said method comprising the steps of:

a) measuring the level of the phospho-Akt proteins in a sample obtained from a patient to obtain a value or values representing this level, said phospho-Akt proteins being selected from the group consisting of phospho-Aktl, phospho-Akt2; and phospho-Akt3, wherein the phospho-Akt proteins contain at least one phosphorylation at a site other than T308 of phospho-Akt1, T309 of phospho-Akt 2, and T305 of phospho-Akt3 respectively; and b) comparing the value or values of the levels from step a) with a standard value or a set of standard values which comparison is predictive of responsiveness to compounds of formula I or pharmaceutically acceptable salts, esters and amides of naturally occurring amino acids, small peptides or pegylated hydroxy acids; salts of such esters and amides; and isomers of the compound of formula I, and wherein said disease is a neoplastic disease selected from the group consisting of epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and glomus tumours, naevi and melanomas, soft tissue tumours and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumours, lymphatic vessel tumours, osseous and chondromatous neoplasms, giant cell tumours, miscellaneous bone tumours, odontogenic tumours, gliomas, neuroepitheliomatous neoplasms, meningiomas, nerve sheath tumours, granular cell tumours and alveolar soft part sarcomas, Hodgkin's and non-Hodgkin's lymphomas, other lymphoreticular neoplasms, plasma cell tumours, mast cell tumours, immunoproliferative diseases, leukemias, miscellaneous myeloproliferative disorders, lymphoproliferative disorders and myelodysplastic syndromes.

20. The method of claim 19 wherein the phospho-Akt proteins are also phosphorylated on the following threonine residue: for phospho-Akt1: T308; for phospho-Akt2: T309; and for phospho-Akt3: T305.

21. The method of claim 19, wherein said patient is an animal or human being and the level of phospho-Akt proteins is measured ex vivo in the sample taken from said animal or human being.

22. The method according to claim 19, wherein the sample is derived from normal tissue, tumor tissue, circulating tumor cells, plasma or whole blood.

23. The method of claim 22, wherein a higher level of phospho-Akt proteins in the sample relative to a standard value or a set of standard values predicts resistance to treating said disease with said compound of formula I or pharmaceutically acceptable salts, esters and amides of naturally occurring amino acids, small peptides or pegylated hydroxy acids; salts of such esters and amides; polymorphs and isomers of the compound of formula I.

24. The method of claim 23, wherein the determination of a higher level of phospho-Akt in said sample obtained from the animal or human being is carried out by comparing the measured phospho-Act protein level in said sample
   i) relative to a standard value or a set of standard values of levels of phospho-Akt proteins from samples of patients with the same tumor histotype; or
   ii) relative to a standard value or a set of standard values of levels of phospho-Akt proteins from a sample or samples of levels of phospho-Akt from normal cells, tissues or body fluids.

25. The method of claim 24, wherein the samples are human.

26. The method of claim 25, wherein the protein sequence of phospho-Akt is selected from the group consisting of SEQ ID No. 1, SEQ ID 2, SEQ ID 3 and homologues, mutant forms, allelic variants, isoforms, splice variants and proteins with sequences having at least 75% identity to SEQ ID 1, SEQ ID 2, or SEQ ID 3.

27. The method of claim 26, wherein the phospho-Akt has been phosphorylated on the following serine residue: for SEQ ID 1: S473; for SEQ ID 2: S474; and for SEQ ID 3: S472.

28. The method of claim 19, wherein the compound is a compound of general formula I wherein
   R represents phenyl or pyridinyl
   wherein phenyl is optionally substituted by one or two substituents independently selected from the group consisting of lower alkyl, lower alkoxy, amino, acetylamino, halogen and nitro; and wherein pyridinyl is optionally substituted by amino or halogen;
   X represents a group C=O;
   $R^1$ represents hydrogen or cyano-lower alkyl;
   $R^2$, $R^3$, $R^4$, $R^5$, and $R^6$ represents hydrogen;
   or pharmaceutically acceptable salts, esters and amides of naturally occurring amino acids, small peptides or pegylated hydroxy acids; salts of such esters and amides; and isomers of the compound of general formula I,
   and wherein the term "lower" denotes a radical having up to a maximum of 7 carbon atoms.

29. The method of claim 23, wherein said neoplastic disease is a cancer.

30. The method according to claim 29, wherein the sample is derived from normal tissue, tumor tissue, circulating tumor cells, plasma or whole blood.

31. The method of claim 30, wherein the determination of a higher level of phospho-Akt in said sample obtained from the animal or human being is carried out by comparing the measured phospho-Akt protein level in said sample
   i) relative to a standard value or a set of standard values of levels of phospho-Akt proteins from samples from other patients having the same tumor histotype as said animal or human being; or
   ii) relative to a standard value or a set of standard values of levels of phospho-Akt proteins from a sample or samples of levels of phospho-Akt proteins from normal tissue.

32. The method of claim 19, wherein the phospho-Akt is used as biomarker to select patients suffering or predisposed to suffering from a disease for treatment with a compound of general formula I as defined in claim 19, or pharmaceutically acceptable salts, esters and amides of naturally occurring amino acids, small peptides or pegylated hydroxy acids; salts of such esters and amides; and isomers of the compound of general formula I.

33. The method of claim 32, wherein the phospho-Akt proteins are used as biomarker to select patients suffering or predisposed to suffering from cancer for treatment with a compound of general formula I or pharmaceutically acceptable salts, esters and amides of naturally occurring amino acids, small peptides or pegylated hydroxy acids; salts of such esters and amides; and isomers of the compound of general formula I.

34. The method of claim 19, wherein the compound is represented by the following formula

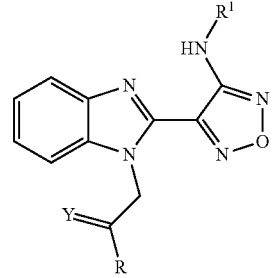

wherein R, Y and R1 are defined as follows:

| R | Y | $R^1$ |
|---|---|---|
| H₂N-⟨phenyl⟩- | O | CH₂CH₂CN |
| H₂N-⟨phenyl⟩- | O | H |
| H₂N-⟨pyridinyl⟩- | O | CH₂CH₂CN | or pharmaceutically acceptable salts, esters and amides of naturally occurring amino acids, small peptides or pegylated hydroxy acids; salts of such esters and amides; and isomers of the compound of general formula I.

35. The method of claim 19, wherein the compound is

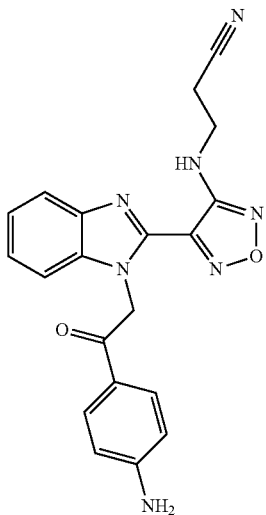 [SMILES: N#CCCNc1nonc1-c1nc2ccccc2n1CC(=O)c1ccc(N)cc1]

or pharmaceutically acceptable salts, esters and amides of naturally occurring amino acids, small peptides or pegylated hydroxy acids; salts of such esters and amides; and isomers of the compound of general formula I.

36. The method of claim 19, wherein the compound is

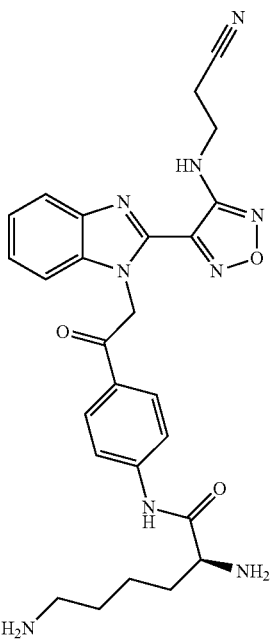

or a pharmaceutically acceptable salt thereof.

37. The method of claim 19 wherein the neoplastic disease is selected from the group consisting of breast cancer, prostate cancer, cervical cancer, ovarian cancer, gastric cancer, colorectal cancer, pancreatic cancer, liver cancer, brain cancer, neuroendocrine cancer, lung cancer, kidney cancer, hematological malignancies, melanoma and sarcomas.

38. The method of claim 37, wherein the neoplastic disease is selected from the group consisting of breast cancer, cervical cancer, gastric cancer, lung cancer, colorectal cancer and melanoma.

39. The method of claim 38, wherein the neoplastic disease is a selected from the group consisting of gastric cancer, colorectal cancer, lung cancer and melanoma.

40. The method of claim 28, wherein said patient is an animal or human being and the level of phospho-Akt proteins is measured ex vivo in the sample taken from said animal or human being.

41. The method of claim 30, wherein a higher level of phospho-Akt proteins in a sample obtained from said animal or human being relative to a standard value or a set of standard values predicts resistance to a therapy with compounds of formula I or pharmaceutically acceptable salts, esters and amides of naturally occurring amino acids, small peptides or pegylated hydroxy acids; salts of such esters and amides; and isomers of the compound of formula I.

42. The method of claim 19, wherein the phospho-Akt proteins are used as biomarker to select subjects suffering or predisposed to suffering from a disease for treatment with a compound of general formula I or with pharmaceutically acceptable salts, esters and amides of naturally occurring amino acids, small peptides or pegylated hydroxy acids; salts of such esters and amides; and isomers of the compound of general formula I.

43. The method of claim 28, wherein the phospho-Akt proteins are used as biomarker to select subjects suffering or predisposed to suffering from cancer for treatment with a compound of general formula I or with pharmaceutically acceptable salts, esters and amides of naturally occurring amino acids, small peptides or pegylated hydroxy acids; salts of such esters and amides; and isomers of the compound of general formula I.

44. The method of claim 1 wherein the neoplastic disease is selected from the group consisting of breast cancer, cervical cancer, gastric cancer, lung cancer, colorectal cancer and melanoma.

45. The method of claim 1 wherein the neoplastic disease is selected from the group consisting of gastric cancer, colorectal cancer, lung cancer and melanoma.

46. The method of claim 1 wherein the neoplastic disease is a cancer selected from cancers in terms of the organs and parts of the body affected, selected from the group consisting of breast, cervicx, ovaries, colon, rectum, lung, endocrine system, bone, adrenal gland, thymus, liver, stomach intestine, pancreas, bone marrow, hematological malignancies, bladder, urinary tract, kidneys, skin, thyroid, brain, head, neck, prostate and testis.

47. The method of claim 19 wherein the neoplastic disease is a cancer selected from cancers in terms of the organs and parts of the body affected, selected from the group consisting of breast, cervicx, ovaries, colon, rectum, lung, endocrine system, bone, adrenal gland, thymus, liver, stomach intestine, pancreas, bone marrow, hematological malignancies, bladder, urinary tract, kidneys, skin, thyroid, brain, head, neck, prostate and testis.

48. The method of claim 1, wherein the sample is derived from tumor tissue or circulating tumor cells.

49. The method of claim 19 wherein the neoplastic disease is selected from the group consisting of breast cancer, cervical cancer, gastric cancer, lung cancer, colorectal cancer and melanoma.

50. The method of claim 19 wherein the neoplastic disease is selected from the group consisting of gastric cancer, colorectal cancer, lung cancer and melanoma.

51. The method according to claim 19, wherein the sample is derived from tumor tissue or circulating tumor cells.

52. The method of claim 35, wherein the neoplastic disease is breast cancer.

53. The method of claim 35, wherein the neoplastic disease is ovarian cancer.

54. The method of claim 35, wherein the neoplastic disease is colorectal cancer.

55. The method of claim 35, wherein the neoplastic disease is lung cancer.

56. The method of claim 35, wherein the neoplastic disease is liver cancer.

57. The method of claim 35, wherein the neoplastic disease is gastric cancer.

58. The method of claim 35, wherein the neoplastic disease is pancreatic cancer.

59. The method of claim 35, wherein the neoplastic disease is a hematological malignancy.

60. The method of claim 35, wherein the neoplastic disease is kidney cancer.

61. The method of claim 35, wherein the neoplastic disease is skin cancer.

62. The method of claim 35, wherein the neoplastic disease is brain cancer.

63. The method of claim 35, wherein the neoplastic disease is prostate cancer.

64. The method of claim 35, wherein the neoplastic disease is head and neck cancer.

65. The method of claim 35, wherein the neoplastic disease is a sarcomas.

66. The method of claim 35, wherein the neoplastic disease is glioma.

67. The method of claim 36, wherein the neoplastic disease is breast cancer.

68. The method of claim 36, wherein the neoplastic disease is ovarian cancer.

69. The method of claim 36, wherein the neoplastic disease is colorectal cancer.

70. The method of claim 36, wherein the neoplastic disease is lung cancer.

71. The method of claim 36, wherein the neoplastic disease is liver cancer.

72. The method of claim 36, wherein the neoplastic disease is gastric cancer.

73. The method of claim 36, wherein the neoplastic disease is pancreatic cancer.

74. The method of claim 36, wherein the neoplastic disease is a hematological malignancy.

75. The method of claim 36, wherein the neoplastic disease is kidney cancer.

76. The method of claim 36, wherein the neoplastic disease is skin cancer.

77. The method of claim 36, wherein the neoplastic disease is brain cancer.

78. The method of claim 36, wherein the neoplastic disease is prostate cancer.

79. The method of claim 36, wherein the neoplastic disease is head and neck cancer.

80. The method of claim 36, wherein the neoplastic disease is a sarcomas.

81. The method of claim 36, wherein the neoplastic disease is glioma.

* * * * *

UNITED STATES PATENT AND TRADEMARK OFFICE
CERTIFICATE OF CORRECTION

PATENT NO. : 10,006,078 B2
APPLICATION NO. : 14/005680
DATED : June 26, 2018
INVENTOR(S) : Heidi Alexandra Lane and Felix Bachmann Page 1 of 1

It is certified that error appears in the above-identified patent and that said Letters Patent is hereby corrected as shown below:

In the Claims

At Column 57, Line 58, "alkyl," should be added after "lower alkoxy-lower.".

At Column 58, Line 13, "aikoxy" should be printed as "alkoxy.".

At Column 59, Line 18, "polymorphs" should be deleted.

At Column 59, Line 53, "represents" should be printed as "represent.".

At Column 62, Line 6, "a" should be deleted.

Signed and Sealed this
Fourth Day of September, 2018

Andrei Iancu
*Director of the United States Patent and Trademark Office*

```
                             SEQUENCE LISTING

<160> NUMBER OF SEQ ID NOS: 3

<210> SEQ ID NO 1
<211> LENGTH: 480
<212> TYPE: PRT
<213> ORGANISM: Homo sapiens

<400> SEQUENCE: 1

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220
```

```
Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
            245                 250                 255

Ile Val Ser Ala Leu Asp Tyr Leu His Ser Glu Lys Asn Val Val Tyr
        260                 265                 270

Arg Asp Leu Lys Leu Glu Asn Leu Met Leu Asp Lys Asp Gly His Ile
    275                 280                 285

Lys Ile Thr Asp Phe Gly Leu Cys Lys Glu Gly Ile Lys Asp Gly Ala
290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
            325                 330                 335

Val Val Met Tyr Glu Met Met Cys Gly Arg Leu Pro Phe Tyr Asn Gln
        340                 345                 350

Asp His Glu Lys Leu Phe Glu Leu Ile Leu Met Glu Glu Ile Arg Phe
    355                 360                 365

Pro Arg Thr Leu Gly Pro Glu Ala Lys Ser Leu Leu Ser Gly Leu Leu
370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
            405                 410                 415

Tyr Glu Lys Lys Leu Ser Pro Pro Phe Lys Pro Gln Val Thr Ser Glu
        420                 425                 430

Thr Asp Thr Arg Tyr Phe Asp Glu Glu Phe Thr Ala Gln Met Ile Thr
    435                 440                 445

Ile Thr Pro Pro Asp Gln Asp Asp Ser Met Glu Cys Val Asp Ser Glu
450                 455                 460

Arg Arg Pro His Phe Pro Gln Phe Ser Tyr Ser Ala Ser Gly Thr Ala
465                 470                 475                 480

<210> SEQ ID NO 2
<211> LENGTH: 481
<212> TYPE: PRT
<213> ORGANISM: Homo sapiens

<400> SEQUENCE: 2

Met Asn Glu Val Ser Val Ile Lys Glu Gly Trp Leu His Lys Arg Gly
1               5                   10                  15

Glu Tyr Ile Lys Thr Trp Arg Pro Arg Tyr Phe Leu Leu Lys Ser Asp
            20                  25                  30

Gly Ser Phe Ile Gly Tyr Lys Glu Arg Pro Glu Ala Pro Asp Gln Thr
        35                  40                  45

Leu Pro Pro Leu Asn Asn Phe Ser Val Ala Glu Cys Gln Leu Met Lys
    50                  55                  60

Thr Glu Arg Pro Arg Pro Asn Thr Phe Val Ile Arg Cys Leu Gln Trp
65                  70                  75                  80

Thr Thr Val Ile Glu Arg Thr Phe His Val Asp Ser Pro Asp Glu Arg
                85                  90                  95

Glu Glu Trp Met Arg Ala Ile Gln Met Val Ala Asn Ser Leu Lys Gln
            100                 105                 110

Arg Ala Pro Gly Glu Asp Pro Met Asp Tyr Lys Cys Gly Ser Pro Ser
```

```
            115                 120                 125
Asp Ser Ser Thr Thr Glu Glu Met Glu Val Ala Val Ser Lys Ala Arg
        130                 135                 140
Ala Lys Val Thr Met Asn Asp Phe Asp Tyr Leu Lys Leu Leu Gly Lys
145                 150                 155                 160
Gly Thr Phe Gly Lys Val Ile Leu Val Arg Glu Lys Ala Thr Gly Arg
                165                 170                 175
Tyr Tyr Ala Met Lys Ile Leu Arg Lys Glu Val Ile Ile Ala Lys Asp
            180                 185                 190
Glu Val Ala His Thr Val Thr Glu Ser Arg Val Leu Gln Asn Thr Arg
                195                 200                 205
His Pro Phe Leu Thr Ala Leu Lys Tyr Ala Phe Gln Thr His Asp Arg
        210                 215                 220
Leu Cys Phe Val Met Glu Tyr Ala Asn Gly Gly Glu Leu Phe Phe His
225                 230                 235                 240
Leu Ser Arg Glu Arg Val Phe Thr Glu Glu Arg Ala Arg Phe Tyr Gly
                245                 250                 255
Ala Glu Ile Val Ser Ala Leu Glu Tyr Leu His Ser Arg Asp Val Val
            260                 265                 270
Tyr Arg Asp Ile Lys Leu Glu Asn Leu Met Leu Asp Lys Asp Gly His
        275                 280                 285
Ile Lys Ile Thr Asp Phe Gly Leu Cys Lys Glu Gly Ile Ser Asp Gly
            290                 295                 300
Ala Thr Met Lys Thr Phe Cys Gly Thr Pro Glu Tyr Leu Ala Pro Glu
305                 310                 315                 320
Val Leu Glu Asp Asn Asp Tyr Gly Arg Ala Val Asp Trp Trp Gly Leu
                325                 330                 335
Gly Val Val Met Tyr Glu Met Met Cys Gly Arg Leu Pro Phe Tyr Asn
            340                 345                 350
Gln Asp His Glu Arg Leu Phe Glu Leu Ile Leu Met Glu Glu Ile Arg
        355                 360                 365
Phe Pro Arg Thr Leu Ser Pro Glu Ala Lys Ser Leu Leu Ala Gly Leu
370                 375                 380
Leu Lys Lys Asp Pro Lys Gln Arg Leu Gly Gly Gly Pro Ser Asp Ala
385                 390                 395                 400
Lys Glu Val Met Glu His Arg Phe Phe Leu Ser Ile Asn Trp Gln Asp
                405                 410                 415
Val Val Gln Lys Lys Leu Leu Pro Pro Phe Lys Pro Gln Val Thr Ser
            420                 425                 430
Glu Val Asp Thr Arg Tyr Phe Asp Asp Glu Phe Thr Ala Gln Ser Ile
        435                 440                 445
Thr Ile Thr Pro Pro Asp Arg Tyr Asp Ser Leu Gly Leu Leu Glu Leu
        450                 455                 460
Asp Gln Arg Thr His Phe Pro Gln Phe Ser Tyr Ser Ala Ser Ile Arg
465                 470                 475                 480
Glu

<210> SEQ ID NO 3
<211> LENGTH: 479
<212> TYPE: PRT
<213> ORGANISM: Homo sapiens

<400> SEQUENCE: 3

Met Ser Asp Val Thr Ile Val Lys Glu Gly Trp Val Gln Lys Arg Gly
```

-continued

```
  1               5                   10                  15
Glu Tyr Ile Lys Asn Trp Arg Pro Arg Tyr Phe Leu Leu Lys Thr Asp
                 20                  25                  30
Gly Ser Phe Ile Gly Tyr Lys Glu Lys Pro Gln Asp Val Asp Leu Pro
             35                  40                  45
Tyr Pro Leu Asn Asn Phe Ser Val Ala Lys Cys Gln Leu Met Lys Thr
         50                  55                  60
Glu Arg Pro Lys Pro Asn Thr Phe Ile Ile Arg Cys Leu Gln Trp Thr
 65                  70                  75                  80
Thr Val Ile Glu Arg Thr Phe His Val Asp Thr Pro Glu Glu Arg Glu
                 85                  90                  95
Glu Trp Thr Glu Ala Ile Gln Ala Val Ala Asp Arg Leu Gln Arg Gln
             100                 105                 110
Glu Glu Glu Arg Met Asn Cys Ser Pro Thr Ser Gln Ile Asp Asn Ile
         115                 120                 125
Gly Glu Glu Glu Met Asp Ala Ser Thr Thr His His Lys Arg Lys Thr
 130                 135                 140
Met Asn Asp Phe Asp Tyr Leu Lys Leu Leu Gly Lys Gly Thr Phe Gly
 145                 150                 155                 160
Lys Val Ile Leu Val Arg Glu Lys Ala Ser Gly Lys Tyr Tyr Ala Met
                 165                 170                 175
Lys Ile Leu Lys Lys Glu Val Ile Ile Ala Lys Asp Glu Val Ala His
             180                 185                 190
Thr Leu Thr Glu Ser Arg Val Leu Lys Asn Thr Arg His Pro Phe Leu
         195                 200                 205
Thr Ser Leu Lys Tyr Ser Phe Gln Thr Lys Asp Arg Leu Cys Phe Val
 210                 215                 220
Met Glu Tyr Val Asn Gly Gly Glu Leu Phe Phe His Leu Ser Arg Glu
 225                 230                 235                 240
Arg Val Phe Ser Glu Asp Arg Thr Arg Phe Tyr Gly Ala Glu Ile Val
                 245                 250                 255
Ser Ala Leu Asp Tyr Leu His Ser Gly Lys Ile Val Tyr Arg Asp Leu
             260                 265                 270
Lys Leu Glu Asn Leu Met Leu Asp Lys Asp Gly His Ile Lys Ile Thr
         275                 280                 285
Asp Phe Gly Leu Cys Lys Glu Gly Ile Thr Asp Ala Ala Thr Met Lys
 290                 295                 300
Thr Phe Cys Gly Thr Pro Glu Tyr Leu Ala Pro Glu Val Leu Glu Asp
 305                 310                 315                 320
Asn Asp Tyr Gly Arg Ala Val Asp Trp Trp Gly Leu Gly Val Val Met
                 325                 330                 335
Tyr Glu Met Met Cys Gly Arg Leu Pro Phe Tyr Asn Gln Asp His Glu
             340                 345                 350
Lys Leu Phe Glu Leu Ile Leu Met Glu Asp Ile Lys Phe Pro Arg Thr
         355                 360                 365
Leu Ser Ser Asp Ala Lys Ser Leu Leu Ser Gly Leu Leu Ile Lys Asp
 370                 375                 380
Pro Asn Lys Arg Leu Gly Gly Gly Pro Asp Asp Ala Lys Glu Ile Met
 385                 390                 395                 400
Arg His Ser Phe Phe Ser Gly Val Asn Trp Gln Asp Val Tyr Asp Lys
                 405                 410                 415
Lys Leu Val Pro Pro Phe Lys Pro Gln Val Thr Ser Glu Thr Asp Thr
             420                 425                 430
```

```
Arg Tyr Phe Asp Glu Glu Phe Thr Ala Gln Thr Ile Thr Ile Thr Pro
        435                 440                 445

Pro Glu Lys Tyr Asp Glu Asp Gly Met Asp Cys Met Asp Asn Glu Arg
    450                 455                 460

Arg Pro His Phe Pro Gln Phe Ser Tyr Ser Ala Ser Gly Arg Glu
465             470                 475
```